United States Patent [19]
Lieschke et al.

[11] Patent Number: 5,891,680
[45] Date of Patent: Apr. 6, 1999

[54] BIOACTIVE FUSION PROTEINS COMPRISING THE P35 AND P40 SUBUNITS OF IL-12

[75] Inventors: Graham J. Lieschke, Cambridge; Richard C. Mulligan, Lincoln, both of Mass.

[73] Assignee: Whitehead Institute for Biomedical Research, Cambridge, Mass.

[21] Appl. No.: 385,335

[22] Filed: Feb. 8, 1995

[51] Int. Cl.$^6$ .............................. C12N 15/19; C07K 14/54
[52] U.S. Cl. .................. 435/69.52; 435/69.5; 435/69.51; 435/69.7; 435/252.3; 435/320.1; 435/325; 530/351; 536/23.4; 536/23.5; 424/88.2; 930/141
[58] Field of Search .......................... 530/351; 536/23.4, 536/23.5; 435/69.52, 69.7, 252.3, 320.1, 240.2, 325

[56] References Cited

U.S. PATENT DOCUMENTS

| | | | |
|---|---|---|---|
| 4,916,212 | 4/1990 | Markussen et al. | 530/303 |
| 4,946,778 | 8/1990 | Ladner et al. | 435/69.7 |
| 5,082,658 | 1/1992 | Palladino | 424/85.2 |
| 5,091,513 | 2/1992 | Huston et al. | 530/387 |
| 5,359,046 | 10/1994 | Capon et al. | 536/23.4 |
| 5,635,599 | 6/1997 | Pastan et al. | 530/351 |
| 5,648,467 | 7/1997 | Trinchieri et al. | 530/351 |
| 5,650,490 | 7/1997 | Gately et al. | 530/351 |
| 5,705,484 | 1/1998 | Thomason | 514/12 |

FOREIGN PATENT DOCUMENTS

| | | |
|---|---|---|
| 2002607 | 5/1990 | Canada . |
| 2032653 | 6/1991 | Canada . |
| A-433827 | 6/1991 | European Pat. Off. . |
| A-614982 | 9/1994 | European Pat. Off. . |
| 0681227 | 10/1994 | European Pat. Off. . |
| 92/05256 | 4/1992 | WIPO . |
| 93/23550 | 11/1993 | WIPO . |
| WO-A-9413806 | 6/1994 | WIPO . |
| 95/00646 | 1/1995 | WIPO . |

OTHER PUBLICATIONS

Callard et al. The Cytokine FactsBook, pp. 214–215, 1994.
Martinotti, et al., "CD4 T cells inhibit in vivo the CD8–mediated immune response against murine colon carcinoma cells transduced with interleukin–12 genes", *Eur. J. Immunol.,* 25:137–146 (1995).
Huston, et al., "Protein engineering of antibody binding sites: Recovery of specific activity in an anti–digoxin single–chain Fv analogue produced in *Escherichia coli*", *Proc. Natl. Acad. Sci. USA,* 85:5879–5883 (1988).
Gubler et al. Proc. Natl. Acad. Sci. USA (1991) 88, 4143–4147.
Gillessen, S., et al., "Mouse interleukin–12 (IL–12) p40 homodimer: a potent IL–12 antagonist," *Eur. J. Immunology* 25:200–206 (1995).
Dranoff, Glenn, et al., "Vaccination with irradiated tumor cells engineered to secrete murine granulocyte–macrophage colony–stimulating factor stimulates potent, specific, and long–lasting anti–tumor immunity," *PNAS* 90:3539–3543 (Apr. 1993).
Trinchieri, Giorgio, "Interleukin–12: A Cytokine Produced by Antigen–Presenting Cells with Immunoregulatory Functions in the Generation of T–Helper Cells Type 1 and Cytotoxic Lymphocytes," *Blood* 84(12):4008–4027 (Dec. 1, 1994).
Pear, Warren S., et al., "Production of high–titer helper–free retroviruses by transient transfection," *PNAS* 90:8392–8396 (Sep. 1993).
Schoenhaut, David S., et al., "Cloning and Expression of Murine IL–12," *J. Immunology* 148(11):3433–3440 (Jun. 1992).

*Primary Examiner*—Garnette D. Draper
*Attorney, Agent, or Firm*—Hamilton, Brook, Smith & Reynolds, P.C.

[57] ABSTRACT

Fusion proteins, such as a bio active IL-12 polypeptide, which comprise at least two polypeptide monomers (chains of amino acids) joined through a heterologous polypeptide linker and which are bioactive, as well as to their production.

20 Claims, 31 Drawing Sheets

A 5'>>>AGC.TCC.GCC.GGT.GGT.GGG.TCG.GGT.GGC.GGA.TCT.TCC.ATG.GGT.CCT.CAG>>>-3'
  IL-12p35    Linker                                              IL-12p40
              Gly.Gly.Gly.Gly.Ser.Gly.Gly.Gly.Gly.Ser.Ser B 5'>>>GTC.CGA.TCC.GGT.GGC.GGT.GGG.TCG.GGT.GGC.GGA.TCT.TCC.ATG.GGT.CAA>>>-3'
  IL-12p40    Linker                                              IL-12p35
              Gly.Gly.Gly.Gly.Ser.Gly.Gly.Gly.Gly.Ser.Ser C 5'>>>AGC.TCC.GCC.GGT.GGC.GGT.GGG.TCG.GGT.GGC.GGA.TCT.ATG.TGG.GAG.CTG>>>-3'
  IL-12p35    Linker                                              ΔIL-12p40
              Gly.Gly.Gly.Gly.Ser.Gly.Gly.Gly.Gly.Ser.Ser

D 5'>>>GTC.CGA.TCC.GGT.GGC.GGT.GGG.TCG.GGT.GGC.GGA.TCT.AGG.G

Positions of Restriction Endonucleases sites (unique sites underlined)

```
                                                                    Rma I
                                                                    Sty I
  Alu I                                                             BsaJ I
  Hind III  Dde I              Fok I                                Avr II    Fau I
  | |       |                  |                                    | |       |
  AAGCTTTGCTCTTAGGAGTTTCCTAATACATCCCAAACTCAAATATATAAAGCATTTGACTTGTTCTATGCCCTAGGGGG   80
  TTCGAAACGAGAATCCTCAAAGGATTATGTAGGGTTTGAGTTTATATATTTCGTAAACTGAACAAGATACGGGATCCCCC
  | |       •|              •  |•        •           •          •  • | |       |
  1         11                 29                                    72        80
   2                                                                 72
                                                                     72
                                                                     73

Dde I
             Esp I
             BspW I                       Dra I                Mse I
             Alu I     Alu I      Mse I   Mse I     Mse I      Dra I
             | | |     |          |       | |       |          | |
  CGGGGGGAAGCTAAGCCAGCTTTTTTTAACATTTAAAATGTTAATTCCATTTTTAAATGCACAGATGTTTTTATTTCATAA    160
  GCCCCCCTTCGATTCGGTCGAAAAAAATTGTAAATTTTACAATTAAGGTAAAATTTACGTGTCTACAAAAATAAAGTATT
             | | |     |       •  | |    •|        •|         •| |       •      •
             89        98         106     113       121        131
             90                           112                  132
             90
             91

Fnu4H I
                              Bbv I
                 Bsm I                               Alu I
                 Nla III   Ssp I       Mae III       Rma I             Mae II      Dde I
                 | |       |           |             | |               |           |
  GGGTTTCAATGTGCATGAATGCTGCAATATTCCTGTTACCAAAGCTAGTATAAATAAAAATAGATAAACGTGGAAATTAC     240
  CCCAAAGTTACACGTACTTACGACGTTATAAGGACAATGGTTTCGATCATATTTATTTTTATCTATTTGCACCTTTAATG
           •     | |     •|            |         •  | |         •                  |
                 174      186           195          205                228         240
                 177                                 203
                 181
                 181

Dde I
                                                        Esp I
                                                        BspW I
                                                        Fnu4H I
                                    Hinc II            Bbv I
                       Mae II  Dde I                   HinP I
                       Mse I   Mnl I                   Hha I           Bsr I   SfaN I
                       |       | |                     | | |           |       |
  TTAGAGTTTCTGTCATTAACGTTTCCTTCCTCAGTTGACAACATAAATGCGCTGCTGAGCAAGCCAGTTTGCATCTGTCA    320
  AATCTCAAAGACAGTAATTGCAAAGGAAGGAGTCAACTGTTGTATTTACGCGACGACTCGTTCGGTCAAACGTAGACAGT
           •     | |•          | |      | •            |•| | |     •  |     •|
                 256            269                    289             304     311
                 259            270                    289
                                274                    291
                                                       291
                                                       294
                                                       294
                                                       295

Sau3A I                                                                Nla III
  Mbo I                                                                  NspC I
  Dpn II                                                                 Nsp7524 I
  Dpn I                              Mse I   Rma I                       Nsp I
  Alw I           Bsr I       Ase I  Spe I                               Afl III
  | |             |           | |    | |                                 | |
  GGATCAATTTCCCATTATGCCAGTCATATTAATTACTAGTCAATTAGTTGATTTTTATTTTTGACATATACATGTGAATG    400
  CCTAGTTAAAGGGTAATACGGTCAGTATAATTAATGATCAGTTAATCAACTAAAAATAAAAACTGTATATGTACACTTAC
  | |         •               | |•   | |         •            •     •   | |
  321                         340    348 355                              390
  322                                 349 356                             390
  322                                                                     390
  322                                                                     390
  322                                                                     391
```

```
                                          HinP I
                                          Hha I                SfaN I
                                          BstU I               Fnu4H I
                                          Fnu4H I              Bbv I
                                          HinP I               Sfe I
                         Sau96 I          Hha I                Pst I
                         Ava II           BstU I    Hga I      Fnu4H I
                         Nla IV           Fnu4H I   BstU I     Bbv I              BsmA I
                          ||               | || |   ||||        ||| |              |
TTTTTGCTTTCGGTTTGGGACCGAAGCCGCGCCGGCGGCGTCTTGTCTGCTGCAGCATCGTTCTGTGTTGTCTCTGTCTGAC   1440
AAAAACGAAAGCCAAACCCTGGCTTCGGCGCGGCGCAGAACAGACGACGTCGTAGCAAGACACAACAGAGACAGACTG
         •          || •     | ||•|  ||||   •       ||  |    •        • |   •
       1377       1386       1395           1407                    1428
       1378      1388        1396           1407
       1378      1389                       1408
                 1389                       1408
                 1391                       1410
                  1393                      1410
                   1394                1413
                   1394
                   ScrF I
                   Nci I
                   Msp I
                   Hpa II
                   Dsa V
                   BstK I
                   Bcn I
                   Xma I
                   Sma I
                   ScrF I
                   Nci I
                   Dsa V
                   BstK I
                   BsaJ I
                   Bcn I
                   Ava I
                   Sau96 I
                   Hae III
                   Sau96 I
                   Nla IV
                   Bsp1286 I
                   Bsp120 I                                             Mae III
                   Ban II          Rma I            Mse I       Dde I
                   Apa I           Nhe I   Mae III  Afl II      Bsu36 I  Bsr I
                   ||•||           ||•      |        ||•         ||  •|  |     •
TGTGTTTCTGTATTTGTCTGAAAATATGGGCCCGGGCTAGCCTGTTACCACTCCCTTAAGTTTGACCTTAGGTCACTGGA    1520
ACACAAGACATAAACAGACTTTTATACCCGGGCCCGATCGGACAATGGTGAGGGAATTCAAACTGGAATCCAGTGACCT
        ||•||           ||•      |        ||•         ||  •|  |     •
        1468           1476     1484     1495        1506       1515
        1468           1477                1496      1507
        1468                                                  1512
        1468
        1468
        1468
        1469
        1469
         1471
         1471
         1471
         1471
         1471
         1471
         1471
         1471
          1472
          1472
          1472
          1472
          1472
          1472
          1472
```

```
                              Bsp1286 I
                              Nla IV
                              Ban I
                    ScrF I              Sau96 I
                    EcoR II             Ava II
                    Dsa V               PpuM I
                    BstN I              EcoO109 I
         Rma I      BstK I     Sty I
         Xba I      BsaJ I     BsaJ I
         |||        |  ||      |  ||
AGCAGTTTCTAGAGAACCATCAGATGTTTCCAGGGTGCCCCAAGGACCTGAAATGACCCTGTGCCTTATTTGAACTAACC   2800
TCGTCAAAGATCTCTTGGTAGTCTACAAAGGTCCCACGGGGTTCCTGGACTTTACTGGACACGGAATAAACTTGATTGG
         ||·        |  ||      |  ||
         2728       2750       2760
         2729       2750       2760
                    2750       2763
                    2750       2763
                    2750       2764
                    2750       2764
                       2754
                       2754
                       2755
```

```
                                                                        HinP I
                                                                        Hha I
                                                                        Nla IV
                                                                        Nar I
                                                                        Kas I
                   HinP I     Sac I                                     Hae II
                   Hha I      HgiA I                                    Ehe I
                   BstU I     Ecl136 I                       Ava I
                   HinP I     Bsp1286 I               Mnl I             Bbe I
                   Hha I      Ban II                  BsiY I            Ban I
                   BssH II    Ava I        Bsp1286 I  BsiY I            Aha II
                   BstU I     BspW I Alu I Ban II
                   ||||       |   ·| ||    ||    ·    ||·     |         ||
AATCAGTTCGCTTCTCGCTTCTGTTCGCGCGCTTCTGCTCCCCGAGCTCAATAAAAGAGCCCACAACCCCTCACTCGGGG   2880
TTAGTCAAGCGAAGAGCGAAGACAAGCGCGCGAAGACGAGGGGCTCGAGTTATTTTCTCGGGTGTTGGGGAGTGAGCCCC
                   ||||·      |  ·| ||     |·         ||·     |         ||
                   2826       2837  2845   2857      2868     2879
                   2827            2841    2857      2869     2879
                   2827             2844             2869     2879
                   2827             2844                 2874 2879
                   2828             2844                      2879
                   2829             2844                      2879
                   2829             2844                      2879
                                                              2879
                                                              2879
                                                              2880
                                                              2880
```

FIG. 3K

```
                              Rsa I
                              Csp6 I
                              Nla IV
                              Kpn I
                              Ban I
                              ScrF I
                              Nci I
                              Msp I
                              Hpa II
                              Dsa V
                              BstK I
                              Xma I
                              Sma I
                              ScrF I
                              Nci I
                              Dsa V
                              BstK I
                              BsaJ I
                              Bcn I                                    BsiY I
                   Ple I      Bcn I                                    Mme I
                   Hinf I     Asp718                          Fok I           BsmA I
         Mnl I     Dde I      Bcn I                  Mnl I    SfaN I          Bsa I
   Bsr I           Tth111 I   Ava I                                           
   |     |         | | •|     | |                    |        | | | |         | |
   CGCCAGTCCTCCGATTGACTGAGTCGCCCGGGTACCCGTGTATCCAATAAACCCTCTTGCAGTTGCATCCGACTTGTGGT  2960
   GCGGTCAGGAGGCTAACTGACTCAGCGGGCCCATGGGCACATAGGTTATTTGGGAGAACGTCAACGTAGGCTGAACACCA
   |     •         | |•|      | |•|| •         •        •        | | ||•       ||•
   2883            2897       2907                     2933     2945          2958
         2888           2899  2907                              2946          2959
                             2901  2911                              2948
                                  2901  2908                              2949
                                       2907
                                       2907
                                       2907
                                       2907
                                       2907
                                       2907
                                       2908
                                       2908
                                       2908
                                       2908
                                       2908
                                       2908
                                          2911
                                          2911
                                          2911
                                            2912
                                            2912
                                                                                NspC I
                                                                                Nsp7524 I
                                                                                Fnu4H I
                                                                                Bbv I
                        Mnl I                         Fau I                     Nla III
           Sty I                                      NspB II                   NspC I    Nla III
           BsiY I       Mnl I                         BsiY I                    Nsp7524 I
           BsaJ I       BsmA I                                                  Nsp I    Nsp I
               Bsa I       Dde I                          
   |       |       | | |   |                         | | |      •    | | •| |           •
   CTCGCTGTTCCTTGGGAGGGTCTCCTCTGAGTGATTGACTACCCGTCAGCGGGGGTCTTTCACACATGCAGCATGTATCA  3040
   GAGCGACAAGGAACCCTCCCAGAGGAGACTCACTAACTGATGGGCAGTCGCCCCCAGAAAGTGTGTACGTCGTACATAGT
          |     |  |  |   | •            •  | | | •    •       | | | •| |           •
          2970       2979      2987              3002              3024     3031
          2970       2980                        3003              3024
          2970            2984                         3007        3024     3032
                  2976                                    3009    3025
                                                                    3028
                                                                    3028
                                                                      3031
                                                                      3031
```

```
                Mnl I
            Sau3A I
            Mbo I
            Dpn II
            Dpn I
            Pvu I                                                Sau3A I
            Mcr I                                Sau3A I          Mbo I
            BsiE I   Sau96 I                     Mbo I            Dpn II
            ||       Ava II      Alu I           Dpn II           Dpn I
            ||       | |         |               Dpn I            |
            ||       | |         |     Alw I Mae III              |
            ||       | |         |     Nla III   Nla III          |
            ||       | |         |     |    ||   |     |          |
acttctgacaacgatcggaggaccgaaggagctaaccgcttttttgcacaacatgggggatcatgtaactcgccttgatc 4800
tgaagactgttgctagcctcctggcttcctcgattggcgaaaaaacgtgttgtaccccctagtacattgagcggaactag
    |  ||      | |         |               •   •   ||• |  •        ,    |
    4732    4740         4750              4772     4782              4797
    4732    4740                                 4778  4785           4797
    4732                                         4779                 4797
    4733                                         4779                 4797
    4733                                         4779
    4733                                         4779
    4733
         4738
                                                                         HinP I
         Msp I                                                           Hha I
         Hpa II                                    Sfe I                 Fsp I
    Nla IV  Alu I                       Mae III    SfaN I                Mae II
    |    |  |                           |          |                     |  ||
gttgggaaccggagctgaatgaagccataccaaacgacgagcgtgacaccacgatgcctgtagcaatggcaacaacgttg 4880
caaccccttggcctcgacttacttcggtatggtttgctgctcgcactgtggtgctacggacatcgttaccgttgttgcaac
    |    |• |       •             •       |   •    |    •    |   •     |   ||
    4805    4813                         4843      4853                4875 4879
         4809                                                               4880
         4809                                                               4880

Msp I
                           Hpa II
                           ScrF I
                           Nci I
                           Dsa V
                           BstK I
         Bsr I             Alu I          Mse I    Fok I
         Mse I             Rma I  Bcn I   Ase I    Bsr I   Mnl I
         | |               |   |  ||      ||       |       |
cgcaaactattaactggcgaactacttactctagcttcccggcaacaattaatagactggatggaggcggataaagttgc 4960
gcgtttgataattgaccgcttgatgaatgagatcgaagggccgttgttaattatctgacctacctccgcctatttcaacg
    |                      •| |  ||•      ||•     |  |•         •
    4890                    4911  4918    4928   4936   4944
         4893                    4913     4929  4939
                                 4918
                                 4918
                                 4918
                                 4918
                                 4919
                                 4919

Msp I
              BspW I
              Sau96 I                          Msp I
              Hae III                          Hpa II
    Sau96 I                             Nla IV Cfr10 I           BstU I
    Ava II    HinP I                    Gsu I  Hph I      BsmA I
              Hha I   Bgl I  Hpa II     |   |  ||  |      Bsa I  |
    |         |   |   |      |          |   |  ||  |      ||     |
aggaccacttctgcgctcggcccttccggctggctggtttattgctgataaatctggagccggtgagcgtggtctcgcg 5040
tcctggtgaagacgcgagccgggaaggccgaccgaccaaataacgactatttagacctcggccactcgcacccagagcgc
    |         |   ||  |      •         •       ||  ||     •||   •
    4962      4973  4980    4986               5014  5022       5032
    4962      4973         4986                5016            5033
                    4979                       5019                5037
                    4979                       5020
                    4980                       5020
                    4986
```

FIG. 3Q

```
                Hae III
         Bsr I
   Fnu4H I  Sau96 I                                              Ple I
    Bbv I   Nla IV           Mnl I                              Hinf I              Fok I
     |      | |||              |                                  |                   |
   gtatcattgcagcactggggccagatggtaagccctcccgtatcgtagttatctacacgacggggagtcaggcaactatg   5120
   catagtaacgtcgtgaccccggtctaccattcgggagggcatagcatcaatagatgtgctgcccctcagtccgttgatac
    |•      |•|||•              •         •         •         •   |                   |
   5049    5057              5074                                5105               5120
   5049    5058                                                  5105
           5054
            5059
            Dde I
           Sau3A I
            Mbo I
            Dpn II              Mnl I
            Dpn I    Nla IV       |         Mse I     Mae III
                     Ban I        |           |         |
              |       |           |           |         |
   gatgaacgaaatagacagatcgctgagataggtgcctcactgattaagcattggtaactgtcagaccaagtttactcata   5200
   ctacttgctttatctgtctagcgactctatccacggagtgactaattcgtaaccattgacagtctggttcaaatgagtat
     •       |       •|          |         •  |         |         •         •
           5138    5151                    5164       5174
           5138    5151
           5138           5155
           5138
                  5143
                                                       Sau3A I
                                                        Mbo I
                                              Rma I     Dpn II
                                            Sau3A I     Dpn I
                                             Mbo I      Alw I
                                             Dpn II     BstY I
                                    Mse I    Dpn I                         Nla III
                         Mse I      Dra I    BstY I   Mbo II               BspH I
                         Dra I      Mse I    Alw I    Hph I                  | |
                          | |        ||        | |      | |                  | |
   tatactttagattgatttaaaacttcatttttaattTaaaaggatctaggtgaagatcctttttgataatctcatgacca   5280
   atatgaaatctaactaaattttgaagtaaaaattaaattttcctagatccacttctaggaaaaactattagagtactggt
    •         ||        •|          •||       •|  |  | ||        •          •||
             5216      5231         5242      5249                         5272
             5217              5235 5242      5252                         5273
                                    5236      5243      5254
                                              5243      5255
                                              5243    •  5255
                                              5243       5255
                                                    5246 5255
                                                         5255
                                                            Sau3A I
                                                             Mbo I       Sau3A I
                                                             Dpn II       Mbo I
                                                  Sau3A I   Mbo II       Dpn II
                                                   Mbo I    BstY I       Dpn I
                             Mae II                Dpn II   Dpn I        Alw I
                             Mse I       Hga I     Dpn I    Alw I        BstY I
                              | |         | |       |        |||          ||
   aaatcccttaacgtgagttttcgttccactgagcgtcagaccccgtagaaaagatcaaaggatcttcttgagatccttt   5360
   tttagggaattgcactcaaaagcaaggtgactcgcagtctggggcatcttttctagtttcctagaagaactctaggaaaa
      |•|         •         |•|         •          |        ||| •         ||
     5288                  5309                  5333      5340         5351
        5291                  5313                 5333      5341         5352
                                                   5333      5340         5352
                                                   5333          5343     5352
                                                              5341        5352
                                                              5341
                                                              5341
```

```
                    Pvu II
                    Fnu4H I
                    Bbv I                              HinP I
        Mse I   Alu I                       BspW I     Mse I
        Ase I   NspB II    Bsr I   Fau I   Hha I    Ase I        Alu I
         ||    |||          |       |       |        ||           |
     tcattaatgcagctggcacgacaggtttcccgactggaaagcgggcagtgagcgcaacgcaattaatgtgagttagctca    6240
     agtaattacgtcgaccgtgctgtccaaagggctgacctttcgcccgtcactcgcgttgcgttaattacactcaatcgagt
         ||    |||    .    .    |     .|    .|    .    |     .    ||     .     |      .
        6163  6170         6193    6201     6212     6222         6235
        6164  6171                     6205     6212     6223
              6169
              6169
              6170
                ScrF I
                EcoR II
                Dsa V
                BstN I
                BstK I
                BsaJ I
         BspW I
         Nla IV                      Msp I
         Ban I                       Hpa II
          ||  ||                      |
     ctcattaggcaccccaggctttacactttatgcttccggctcgtatgttgtgtggaattgtgagcggataacaatttcac    6320
     gagtaatccgtggggtccgaaatgtgaaatacgaaggccgagcatacaacacaccttaacactcgcctattgttaaagtg
          ||.  ||    .    .    .    .     |     .     .     .     .     .     .     .
         6248                              6276
         6248                              6276
         6249
          6253
           6254
           6254
           6254
           6254
           6254
         Alu I    Nla III
          |        |
     acaggaaacagctatgaccatgattacgcc   6350
     tgtcctttgtcgatactggtactaatgcgg
          |        |.              .
         6330     6339
```

FIG. 3U

```
    1   aagcttgggctgcaggtcgatcgactctagaggatcgatccccaccATGgGTCAATCACG
        ---------+---------+---------+---------+---------+---------+  60
        ttcgaacccgacgtccagctagctgagatctcctagctaggggtggTACcCAGTTAGTGC MetGlyGlnSerArg -

CTACCTCCTCTTTTTGGCCAACCTTGCCCTCCTAAACCACCTCAGTTTGGCCAGGGTCAT
   61   ---------+---------+---------+---------+---------+---------+ 120
        GATGGAGGAGAAAAACCGGTTGGAACGGGAGGATTTGGTGGAGTCAAACCGGTCCCAGTA

TyrLeuLeuPheLeuAlaThrLeuAlaLeuLeuAsnHisLeuSerLeuAlaArgValIle -

TCCAGTCTCTGGACCTGCCAGGTGTCTTAGCCAGTCCCGAAACCTGCTGAAGACCACAGA
  121   ------------------------------------------------------------ 180
        AGGTCAGAGACCTGGACGGTCCACAGAATCGGTCAGGGCTTTGGACGACTTCTGGTGTCT

ProValSerGlyProAlaArgCysLeuSerGlnSerArgAsnLeuLeuLyThrThrAsp -

TGACATGGTGAAGACGGCCAGAGAAAAACTGAAACATTATTCCTGCACTGCTGAAGACAT
  181   ---------+---------+---------+---------+---------+---------+ 240
        ACTGTACCACTTCTGCCGGTCTCTTTTTGACTTTGTAATAAGGACGTGACGACTTCTGTA

AspMetValLysThrAlaArgGluLysLeuLysHisTyrSerCysThrAlaGluAspIle -
```

FIG. 4A

```
        CGATCATGAAGACATCACACGGGACCAAACCAGCACATTGAAGACCTGTTTACCACTGGA
241     ---------+---------+---------+---------+---------+---------+ 300
        GCTAGTACTTCTGTAGTGTGCCCTGGTTTGGTCGTGTAACTTCTGGACAAATGGTGACCT

AspHisGluAspIleThrArgAspGlnThrSerThrLeuLysThrCysLeuProLeuGlu -

ACTACACAAGAACGAGAGTTGCCTGGCTACTAGAGAGACTTCTTCCACAACAAGAGGGAG
301     ---------+---------+---------+---------+---------+---------+ 360
        TGATGTGTTCTTGCTCTCAACGGACCGATGATCTCTCTGAAGAAGGTGTTGTTCTCCCTC

LeuHisLysAsnGluSerCysLeuAlaThrArgGluThrSerSerThrThrArgGlySer -

CTGCCTGCCCCCACAGAAGACGTCTTTGATGATGACCCTGTGCCTTGGTAGCATCTATGA
361     ---------+---------+---------+---------+---------+---------+ 420
        GACGGACGGGGGTGTCTTCTGCAGAAACTACTACTGGGACACGGAACCATCGTAGATACT

CysLeuProProGlnLysThrSerLeuMetMetThrLeuCysLeuGlySerIleTyrGlu -

GGACTTGAAGATGTACCAGACAGAGTTCCAGGCCATCAACGCAGCACTTCAGAATCACAA
421     ---------+---------+---------+---------+---------+---------+ 480
        CCTGAACTTCTACATGGTCTGTCTCAAGGTCCGGTAGTTGCGTCGTGAAGTCTTAGTGTT

AspLeuLysMetTyrGlnThrGluPheGlnAlaIleAsnAlaAlaLeuGlnAsnHisAsn -

CCATCAGCAGATCATTCTAGACAAGGGCATGCTGGTGGCCATCGATGAGCTGATGCAGTC
481     ---------+---------+---------+---------+---------+---------+ 540
        GGTAGTCGTCTAGTAAGATCTGTTCCCGTACGACCACCGGTAGCTACTCGACTACGTCAG

HisGlnGlnIleIleLeuAspLysGlyMetLeuValAlaIleAspGluLeuMetGlnSer -
```

FIG. 4B

```
            TCTGAATCATAATGGCGAGACTCTGCGCCAGAAACCTCCTGTGGGAGAAGCAGACCCTTA
    541     ---------+---------+---------+---------+---------+---------+ 600
            AGACTTAGTATTACCGCTCTGAGACGCGGTCTTTGGAGGACACCCTCTTCGTCTGGGAAT

LeuAsnHisAsnGlyGluThrLeuArgGlnLysProProValGlyGluAlaAspProTyr -

CAGATGAAAATGAAGCTGTGCATCCTGCTTCACGCCTTCAGCACCCGCGTCGTGACCAT
    601     ---------+---------+---------+---------+---------+---------+ 660
            GTCTCACTTTTACTTCGAGACGTAGGACGAAGTGCGGAAGTCGTGGGCGCAGCACTGGTA

ArgValLysMetLysLeuCysIleLeuLeuHisAlaPheSerThrArgValValThrIle -

CAACAGGGTGATGGGCTATCTGAGCTCCGCCTGAgaattcattgatccactag
    661     ---------+---------+---------+---------+---------+---- 713
            GTTGTCCCACTACCCGATAGACTCGAGGCGGACTcttaagtaactaggtgatc AsnArgValMetGlyTyrLeuSerSerAlaEnd
```

FIG. 4C

```
       AAGCTTGGGCTGCAGGTCGATCGACTCTAGAGGATCGATCCCCACCATGGGTCCTCAGAA
  1    ---------+---------+---------+---------+---------+---------+  60
       TTCGAACCCGACGTCCAGCTAGCTGAGATCTCCTAGCTAGGGGTGGTACCCAGGAGTCTT

MetGlyProGlnLys -

GCTAACCATCTCCTGGTTTGCCATCGTTTTGCTGGTGTCTCCACTCATGGCCATGTGGGA
  61   ---------+---------+---------+---------+---------+---------+ 120
       CGATTGGTAGAGGACCAAACGGTAGCAAAACGACCACAGAGGTGAGTACCCGTACACCT

LeuThrIleSerTrpPheAlaIleValLeuLeuValSerProLeuMetAlaMetTrpGlu -

GCTGGAGAAAGACGTTTATGTTGTAGAGGTGGACTGGACTCCCGATGCCCCTGGAGAAAC
 121   ---------+---------+---------+---------+---------+---------+ 180
       CGACCTCTTTCTGCAAATACAACATCTCCACCTGACCTGAGGGCTACGGGGACCTCTTTG

LeuGluLysAspValTyrValValGluValAspTrpThrProAspAlaProGlyGluThr -

AGTGAACCTCACCTGTGACACGCCTGAAGAAGATGACATCACCTGGACCTCAGACCAGAG
 181   ---------+---------+---------+---------+---------+---------+ 240
       TCACTTGGAGTGGACACTGTGCGGACTTCTTCTACTGTAGTGGACCTGGAGTCTGGTCTC

ValAsnLeuThrCysAspThrProGluGluAspAspIleThrTrpThrSerAspGlnArg-
```

FIG. 5A

```
      ACATGGAGTCATAGGCTCTGGAAAGACCCTGACCATCACTGTCAAAGAGTTTCTAGATGC
241   ---------+---------+---------+---------+---------+---------+ 300
      TGTACCTCAGTATCCGAGACCTTTCTGGGACTGGTAGTGACAGTTTCTCAAAGATCTACG

HisGlyValIleGlySerGlyLysThrLeuThrIleThrValLysGluPheLeuAspAla -

TGGCCAGTACACCTGCACAAAGGAGGCGAGACTCTGAGCCACTCACATCTGCTGCTCCA
301   ---------+---------+---------+---------+---------+---------+ 360
      ACCGGTCATGTGGACGGTGTTTCCTCCGCTCTGAGACTCGGTGAGTGTAGACGACGAGGT

GlyGlnTyrThrCysHisLysGlyGlyGluThrLeuSerHisSerHisLeuLeuLeuHis -

CAAGAAGGAAAATGGAATTTGGTCCACTGAAATTTTAAAAAATTTCAAAAACAAGACTTT
361   ---------+---------+---------+---------+---------+---------+ 420
      AGGTCAGAGACCTGGACGGTCCACAGAATCGGTCAGGGCTTTGGACGACTTCTGGTGTCT

LysLysGluAsnGlyIleTrpSerThrGluIleLeuLysAsnPheLysAsnLysThrPhe -

CCTGAAGTGTGAAGCACCAAATTACTCCGGACGGTTCACGTGCTCATGGCTGGTGCAAAG
421   ---------+---------+---------+---------+---------+---------+ 480
      GGACTTCACACTTCGTGGTTTAATGAGGCCTGCCAAGTGCACGAGTACCGACCACGTTTC

LeuLysCysGluAlaProAsnTyrSerGlyArgPheThrCysSerTrpLeuValGlnArg -
```

FIG. 5B

```
     AAACATGGACTTGAAGTTCAACATCAAGAGCAGTAGCAGTTCCCCTGACTCTCGGGCAGT
481  ---------+---------+---------+---------+---------+---------+ 540
     TTTGTACCTGAACTTCAAGTTGTAGTTCTCGTCATCGTCAAGGGGACTGAGAGCCCGTCA

AsnMetAspLeuLysPheAsnIleLysSerSerSerSerProAspSerArgAlaVal    -

GACATGTGGAATGGCGTCTCTGTCTGCAGAGAAGGTCACACTGGACCAAAGGGACTATGA
541  ---------+---------+---------+---------+---------+---------+ 600
     CTGTACACCTTACCGCAGAGACAGACGTCTCTTCCAGTGTGACCTGGTTTCCCTGATACT

ThrCysGlyMetAlaSerLeuSerAlaGluLysValThrLeuAspGlnArgAspTyrGlu -

GAAGTATTCAGTGTCCTGCCAGGAGGATGTCACCTGCCCAACTGCCGAGGAGACCCTGCC
601  ---------+---------+---------+---------+---------+---------+ 660
     CTTCATAAGTCACAGGACGGTCCTCCTACAGTGGACGGGTTGACGGCTCCTCTGGGACGG

LysTyrSerValSerCysGlnGluAspValThrCysProThrAlaGluGluThrLeuPro -

CATTGAACTGGCGTTGGAAGCACGGCAGCAGAATAAATATGAGAACTACAGCACCAGCTT
661  ---------+---------+---------+---------+---------+---------+ 720
     GTAACTTGACCGCAACCTTCGTGCCGTCGTCTTATTTATACTCTTGATGTCGTGGTCGAA

IleGluLeuAlaLeuGluAlaArgGlnGlnAsnLysTyrGluAsnTyrSerThrSerPhe -

CTTCATCAGGGACATCATCAAACCAGACCCGCCCAAGAACTTGCAGATGAAGCCTTTGAA
721  ---------+---------+---------+---------+---------+---------+ 780
     GAAGTAGTCCCTGTAGTAGTTTGGTCTGGGCGGGTTCTTGAACGTCTACTTCGGAAACTT

PheIleArgAspIleIleLysProAspProProLysAsnLeuGlnMetLysProLeuLys -
```

FIG. 5C

```
       GAACTCACAGGTGGAGGTCAGCTGGGAGTACCCTGACTCCTGGAGCACTCCCCATTCCTA
781    ---------+---------+---------+---------+---------+---------+ 840
       CTTGAGTGTCCACCTCCAGTCGACCCTCATGGGACTGAGGACCTCGTGAGGGGTAAGGAT

AsnSerGlnValGluValSerTrpGluTyrProAspSerTrpSerThrProHisSerTyr   -

CTTCTCCCTCAAGTTCTTTGTTCGAATCCAGCGCAAGAAAGAAAAGATGAAGGAGACAGA
841    ---------+---------+---------+---------+---------+---------+ 900
       GAAGAGGGAGTTCAAGAAACAAGCTTAGGTCGCGTTCTTTCTTTTCTACTTCCTCTGTCT

PheSerLeuLysPhePheValArgIleGlnArgLysLysGluLysMetLysGluThrGlu   -

GGAGGGGTGTAACCAGAAAGGTGCGTTCCTCGTAGAGAAGACATCTACCGAAGTCCAATG
901    ---------+---------+---------+---------+---------+---------+ 960
       CCTCCCCACATTGGTCTTTCCACGCAAGGAGCATCTCTTCTGTAGATGGCTTCAGGTTAC

GluGlyCysAsnGlnLysGlyAlaPheLeuValGluLysThrSerThrGluValGlnCys   -

CAAAGGCGGGAATGTCTGCGTGCAAGCTCAGGATCGCTATTACAATTCCTCATGCAGCAA
961    ---------+---------+---------+---------+---------+---------+1020
       GTTTCCGCCCTTACAGACGCACGTTCGAGTCCTAGCGATAATGTTAAGGAGTACGTCGTT

LysGlyGlyAsnValCysValGlnAlaGlnAspArgTyrTyrAsnSerSerCysSerLys   -

GTGGGCATGTGTTCCCTGCAGGGTCCGATCCTAGGAATTCC
1021   ---------+---------+---------+---------+- 1061
       CACCCGTACACAAGGGACGTCCCAGGCTAGGATCTTAAGG

TrpAlaCysValProCysArgValArgSerEnd
```

FIG. 5D

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 54 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:1:

```
AGCTCCGCCG  GTGGTGGTGG  GTCGGGTGGC  GGCGGATCTT  CCATGGGTCC  TCAG        54
```

( 2 ) INFORMATION FOR SEQ ID NO:2:

( i ) SEQUENCE CHARACTERISTICS:
        ( A ) LENGTH: 66 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:2:

```
GTCCGATCCG  GTGGCGGTGG  CTCGGGCGGT  GGTGGGTCGG  GTGGCGGCGG  ATCTTCCATG   60
GGTCAA                                                                  66
```

( 2 ) INFORMATION FOR SEQ ID NO:3:

(  i  ) SEQUENCE CHARACTERISTICS:
   ( A ) LENGTH: 66 base pairs
   ( B ) TYPE: nucleic acid
   ( C ) STRANDEDNESS: unknown
   ( D ) TOPOLOGY: unknown (  i i  ) MOLECULE TYPE: DNA (genomic)

(  x i  ) SEQUENCE DESCRIPTION: SEQ ID NO:3:

AGCTCCGCCG GTGGCGGTGG CTCGGGCGGT GGTGGGTCGG GTGGCGGCGG ATCTATGTGG  60

GAGCTG  66

( 2 ) INFORMATION FOR SEQ ID NO:4:

(  i  ) SEQUENCE CHARACTERISTICS:
   ( A ) LENGTH: 66 base pairs
   ( B ) TYPE: nucleic acid
   ( C ) STRANDEDNESS: unknown
   ( D ) TOPOLOGY: unknown (  i i  ) MOLECULE TYPE: DNA (genomic)

(  x i  ) SEQUENCE DESCRIPTION: SEQ ID NO:4:

GTCCGATCCG GTGGCGGTGG CTCGGGCGGT GGTGGGTCGG GTGGCGGCGG ATCTAGGGTC  60

ATTCCA  66

( 2 ) INFORMATION FOR SEQ ID NO:5:

(  i  ) SEQUENCE CHARACTERISTICS:
   ( A ) LENGTH: 11 amino acids
   ( B ) TYPE: amino acid
   ( C ) STRANDEDNESS: unknown
   ( D ) TOPOLOGY: unknown (  i i  ) MOLECULE TYPE: protein (  x i  ) SEQUENCE DESCRIPTION: SEQ ID NO:5:

Gly Gly Gly Gly Ser Gly Gly Gly Gly Ser Ser
1               5                   10

( 2 ) INFORMATION FOR SEQ ID NO:6:

(  i  ) SEQUENCE CHARACTERISTICS:
   ( A ) LENGTH: 16 amino acids
   ( B ) TYPE: amino acid
   ( C ) STRANDEDNESS: unknown
   ( D ) TOPOLOGY: unknown (  i i  ) MOLECULE TYPE: protein (  x i  ) SEQUENCE DESCRIPTION: SEQ ID NO:6:

Gly Gly Gly Gly Ser Gly Gly Gly Gly Ser Gly Gly Gly Gly Ser Ser
1               5                   10                  15

( 2 ) INFORMATION FOR SEQ ID NO:7:

(  i  ) SEQUENCE CHARACTERISTICS:
   ( A ) LENGTH: 15 amino acids
   ( B ) TYPE: amino acid
   ( C ) STRANDEDNESS: unknown
   ( D ) TOPOLOGY: unknown (  i i  ) MOLECULE TYPE: protein (  x i  ) SEQUENCE DESCRIPTION: SEQ ID NO:7:

Gly Gly Gly Gly Ser Gly Gly Gly Gly Ser Gly Gly Gly Gly Ser
1               5                   10                  15

( 2 ) INFORMATION FOR SEQ ID NO:8:

( i ) SEQUENCE CHARACTERISTICS:
        ( A ) LENGTH: 6350 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:8:

```
AAGCTTTGCT   CTTAGGAGTT   TCCTAATACA   TCCCAAACTC   AAATATATAA   AGCATTTGAC     60
TTGTTCTATG   CCCTAGGGGG   CGGGGGGAAG   CTAAGCCAGC   TTTTTTTAAC   ATTTAAAATG    120
TTAATTCCAT   TTTAAATGCA   CAGATGTTTT   TATTTCATAA   GGGTTTCAAT   GTGCATGAAT    180
GCTGCAATAT   TCCTGTTACC   AAAGCTAGTA   TAAATAAAAA   TAGATAAACG   TGGAAATTAC    240
TTAGAGTTTC   TGTCATTAAC   GTTTCCTTCC   TCAGTTGACA   ACATAAATGC   GCTGCTGAGC    300
AAGCCAGTTT   GCATCTGTCA   GGATCAATTT   CCCATTATGC   CAGTCATATT   AATTACTAGT    360
CAATTAGTTG   ATTTTTATTT   TTGACATATA   CATGTGAATG   AAAGACCCCA   CCTGTAGGTT    420
TGGCAAGCTA   GCTTAAGTAA   CGCCATTTTG   CAAGGCATGG   AAAAATACAT   AACTGAGAAT    480
AGAAAAGTTC   AGATCAAGGT   CAGGAACAGA   TGGAACAGCT   GAATATGGGC   CAAACAGGAT    540
ATCTGTGGTA   AGCAGTTCCT   GCCCCGGCTC   AGGGCCAAGA   ACAGATGGAA   CAGCTGAATA    600
TGGGCCAAAC   AGGATATCTG   TGGTAAGCAG   TTCCTGCCCC   GGCTCAGGGC   CAAGAACAGA    660
TGGTCCCCAG   ATGCGGTCCA   GCCCTCAGCA   GTTCTAGAG    AACCATCAGA   TGTTTCCAGG    720
GTGCCCCAAG   GACCTGAAAT   GACCCTGTGC   CTTATTTGAA   CTAACCAATC   AGTTCGCTTC    780
TCGCTTCTGT   TCGCGCGCTT   ATGCTCCCCG   AGCTCAATAA   AAGAGCCCAC   AACCCCTCAC    840
TCGGGGCGCC   AGTCCTCCGA   TTGACTGAGT   CGCCCGGGTA   CCCGTGTATC   CAATAAACCC    900
TCTTGCAGTT   GCATCCGACT   TGTGGTCTCG   CTGTTCCTTG   GGAGGGTCTC   CTCTGAGTGA    960
TTGACTACCC   GTCAGCGGGG   GTCTTTCATT   TGGGGGCTCG   TCCGGATCG    GGAGACCCCT   1020
GCCCAGGGAC   CACCGACCCA   CCACCGGGAG   GTAAGCTGGC   CAGCAACTTA   TCTGTGTCTG   1080
TCCGATTGTC   TAGTGTCTAT   GACTGATTTT   ATGCGCCTGC   GTCGGTACTA   GTTAGCTAAC   1140
TAGCTCTGTA   TCTGGCGGAC   CCGTGGTGGA   ACTGACGAGT   TCGGAACACC   CGGCCGCAAC   1200
CCTGGGAGAC   GTCCCAGGGA   CTTCGGGGGC   CGTTTTTGTG   GCCCGACCTG   AGTCCTAAAA   1260
TCCCGATCGT   TTAGGACTCT   TTGGTGCACC   CCCCTTAGAG   GAGGGATATG   TGGTTCTGGT   1320
AGGAGACGAG   AACCTAAAAC   AGTTCCCGCC   TCCGTCTGAA   TTTTTGCTTT   CGGTTTGGGA   1380
CCGAAGCCGC   GCCGCGCGTC   TTGTCTGCTG   CAGCATCGTT   CTGTGTTGTC   TCTGTCTGAC   1440
TGTGTTTCTG   TATTTGTCTG   AAAATATGGG   CCCGGGCTAG   CCTGTTACCA   CTCCCTTAAG   1500
TTTGACCTTA   GGTCACTGGA   AAGATGTCGA   GCGGATCGCT   CACAACCAGT   CGGTAGATGT   1560
CAAGAAGAGA   CGTTGGGTTA   CCTTCTGCTC   TGCAGAATGG   CCAACCTTTA   ACGTCGGATG   1620
GCCGCGAGAC   GGCACCTTTA   ACCGAGACCT   CATCACCCAG   GTTAAGATCA   AGGTCTTTTC   1680
ACCTGGCCCG   CATGGACACC   CAGACCAGGT   GGGGTACATC   GTGACCTGGG   AAGCTTGGC    1740
TTTTGACCCC   CCTCCCTGGG   TCAAGCCCTT   TGTACACCCT   AAGCCTCCGC   CTCCTCTTCC   1800
TCCATCCGCC   CCGTCTCTCC   CCCTTGAACC   TCCTCGTTCG   ACCCCGCCTC   GATCCTCCCT   1860
TTATCCAGCC   CTCACTCCTT   CTCTAGGCGC   CCCCATATGG   CCATATGAGA   TCTTATATGG   1920
GGCACCCCCG   CCCCTTGTAA   ACTTCCCTGA   CCCTGACATG   ACAAGAGTTA   CTAACAGCCC   1980
CTCTCTCCAA   GCTCACTTAC   AGGCTCTCTA   CTTAGTCCAG   CACGAAGTCT   GGAGACCTCT   2040
```

| | | | | | |
|---|---|---|---|---|---|
| GGCGGCAGCC | TACCAAGAAC | AACTGGACCG | ACCGGTGGTA | CCTCACCCTT | ACCGAGTCGG | 2100
| CGACACAGTG | TGGGTCCGCC | GACACCAGAC | TAAGAACCTA | GAACCTCGCT | GGAAAGGACC | 2160
| TTACACAGTC | CTGCTGACCA | CCCCCACCGC | CCTCAAAGTA | GACGGCATCG | CAGCTTGGAT | 2220
| ACACGCCGCC | CACGTGAAGG | CTGCCGACCC | CGGGGGTGGA | CCATCCTCTA | GACTGCCATG | 2280
| GCGCGGATCC | GGATTAGTCC | AATTTGTTAA | AGACAGGATA | TCAGTGGTCC | AGGCTCTAGT | 2340
| TTTGACTCAA | CAATATCACC | AGCTGAAGCC | TATAGAGTAC | GAGCCATAGA | TAAAATAAAA | 2400
| GATTTTATTT | AGTCTCCAGA | AAAAGGGGGG | AATGAAAGAC | CCCACCTGTA | GGTTTGGCAA | 2460
| GCTAGCTTAA | GTAACGCCAT | TTTGCAAGGC | ATGGAAAAAT | ACATAACTGA | GAATAGAGAA | 2520
| GTTCAGATCA | AGGTCAGGAA | CAGATGGAAC | AGCTGAATAT | GGGCCAAACA | GGATATCTGT | 2580
| GGTAAGCAGT | TCCTGCCCCG | GCTCAGGGCC | AAGAACAGAT | GGAACAGCTG | AATATGGGCC | 2640
| AAACAGGATA | TCTGTGGTAA | GCAGTTCCTG | CCCCGGCTCA | GGGCCAAGAA | CAGATGGTCC | 2700
| CCAGATGCGG | TCCAGCCCTC | AGCAGTTTCT | AGAGAACCAT | CAGATGTTTC | CAGGGTGCCC | 2760
| CAAGGACCTG | AAATGACCCT | GTGCCTTATT | TGAACTAACC | AATCAGTTCG | CTTCTCGCTT | 2820
| CTGTTCGCGC | GCTTCTGCTC | CCCGAGCTCA | ATAAAGAGC | CCACAACCCC | TCACTCGGGG | 2880
| CGCCAGTCCT | CCGATTGACT | GAGTCGCCCG | GGTACCCGTG | TATCCAATAA | ACCCTCTTGC | 2940
| AGTTGCATCC | GACTTGTGGT | CTCGCTGTTC | CTTGGGAGGG | TCTCCTCTGA | GTGATTGACT | 3000
| ACCCGTCAGC | GGGGGTCTTT | CACACATGCA | GCATGTATCA | AAATTAATTT | GGTTTTTTTT | 3060
| CTTAAGTATT | TACATTAAAT | GGCCATAGTA | CTTAAAGTTA | CATTGGCTTC | CTTGAAATAA | 3120
| ACATGGAGTA | TTCAGAATGT | GTCATAAATA | TTTCTAATTT | TAAGATAGTA | TCTCCATTGG | 3180
| CTTTCTACTT | TTTCTTTTAT | TTTTTTTGT | CCTCTGTCTT | CCATTGTTG | TTGTTGTTGT | 3240
| TTGTTTGTTT | GTTTGTTGGT | TGGTTGGTTA | ATTTTTTTT | AAAGATCCTA | CACTATAGTT | 3300
| CAAGCTAGAC | TATTAGCTAC | TCTGTAACCC | AGGGTGACCT | TGAAGTCATG | GGTAGCCTGC | 3360
| TGTTTTAGCC | TTCCCACATC | TAAGATTACA | GGTATGAGCT | ATCATTTTG | GTATATTGAT | 3420
| TGATTGATTG | ATTGATGTGT | GTGTGTGTGA | TTGTGTTTGT | GTGTGTGACT | GTGAAAATGT | 3480
| GTGTATGGGT | GTGTGTGAAT | GTGTGTATGT | ATGTGTGTGT | GTGAGTGTGT | GTGTGTGTGT | 3540
| GTGCATGTGT | GTGTGTGTGA | CTGTGTCTAT | GTGTATGACT | GTGTGTGTGT | GTGTGTGTGT | 3600
| GTGTGTGTGT | GTGTGTGTGT | GTGTGTTGTG | AAAAAATATT | CTATGGTAGT | GAGAGCCAAC | 3660
| GCTCCGGCTC | AGGTGTCAGG | TTGGTTTTTG | AGACAGAGTC | TTTCACTTAG | CTTGGAATTC | 3720
| ACTGGCCGTC | GTTTTACAAC | GTCGTGACTG | GGAAAACCCT | GGCGTTACCC | AACTTAATCG | 3780
| CCTTGCAGCA | CATCCCCCTT | TCGCCAGCTG | GCGTAATAGC | GAAGAGGCCC | GCACCGATCG | 3840
| CCCTTCCCAA | CAGTTGCGCA | GCCTGAATGG | CGAATGGCGC | CTGATGCGGT | ATTTTCTCCT | 3900
| TACGCATCTG | TGCGGTATTT | CACACCGCAT | ATGGTGCACT | CTCAGTACAA | TCTGCTCTGA | 3960
| TGCCGCATAG | TTAAGCCAGC | CCCGACACCC | GCCAACACCC | GCTGACGCGC | CCTGACGGGC | 4020
| TTGTCTGCTC | CCGGCATCCG | CTTACAGACA | AGCTGTGACC | GTCTCCGGGA | GCTGCATGTG | 4080
| TCAGAGGTTT | TCACCGTCAT | CACCGAAACG | CGCGATGACG | AAAGGGCCTC | GTGATACGCC | 4140
| TATTTTTATA | GGTTAATGTC | ATGATAATAA | TGGTTTCTTA | GACGTCAGGT | GGCACTTTTC | 4200
| GGGGAAATGT | GCGCGGAACC | CCTATTTGTT | TATTTTTCTA | AATACATTCA | AATATGTATC | 4260
| CGCTCATGAG | ACAATAACCC | TGATAAATGC | TTCAATAATA | TTGAAAAAGG | AAGAGTATGA | 4320
| GTATTCAACA | TTTCCGTGTC | GCCCTTATTC | CCTTTTTTGC | GGCATTTTGC | CTTCCTGTTT | 4380
| TTGCTCACCC | AGAAACGCTG | GTGAAAGTAA | AAGATGCTGA | AGATCAGTTG | GGTGCACGAG | 4440

-continued

| | | | | | |
|---|---|---|---|---|---|
| TGGGTTACAT | CGAACTGGAT | CTCAACAGCG | GTAAGATCCT | TGAGAGTTTT | CGCCCCGAAG 4500 |
| AACGTTTTCC | AATGATGAGC | ACTTTTAAAG | TTCTGCTATG | TGGCGCGGTA | TTATCCCGTA 4560 |
| TTGACGCCGG | GCAAGAGCAA | CTCGGTCGCC | GCATACACTA | TTCTCAGAAT | GACTTGGTTG 4620 |
| AGTACTCACC | AGTCACAGAA | AAGCATCTTA | CGGATGGCAT | GACAGTAAGA | GAATTATGCA 4680 |
| GTGCTGCCAT | AACCATGAGT | GATAACACTG | CGGCCAACTT | ACTTCTGACA | ACGATCGGAG 4740 |
| GACCGAAGGA | GCTAACCGCT | TTTTTGCACA | ACATGGGGGA | TCATGTAACT | CGCCTTGATC 4800 |
| GTTGGGAACC | GGAGCTGAAT | GAAGCCATAC | CAAACGACGA | GCGTGACACC | ACGATGCCTG 4860 |
| TAGCAATGGC | AACAACGTTG | CGCAAACTAT | TAACTGGCGA | ACTACTTACT | CTAGCTTCCC 4920 |
| GGCAACAATT | AATAGACTGG | ATGGAGGCGG | ATAAAGTTGC | AGGACCACTT | CTGCGCTCGG 4980 |
| CCCTTCCGGC | TGGCTGGTTT | ATTGCTGATA | AATCTGGAGC | CGGTGAGCGT | GGGTCTCGCG 5040 |
| GTATCATTGC | AGCACTGGGG | CCAGATGGTA | AGCCCTCCCG | TATCGTAGTT | ATCTACACGA 5100 |
| CGGGGAGTCA | GGCAACTATG | GATGAACGAA | ATAGACAGAT | CGCTGAGATA | GGTGCCTCAC 5160 |
| TGATTAAGCA | TTGGTAACTG | TCAGACCAAG | TTTACTCATA | TATACTTTAG | ATTGATTTAA 5220 |
| AACTTCATTT | TTAATTTAAA | AGGATCTAGG | TGAAGATCCT | TTTTGATAAT | CTCATGACCA 5280 |
| AAATCCCTTA | ACGTGAGTTT | TCGTTCCACT | GAGCGTCAGA | CCCCGTAGAA | AAGATCAAAG 5340 |
| GATCTTCTTG | AGATCCTTTT | TTTCTGCGCG | TAATCTGCTG | CTTGCAAACA | AAAAACCAC 5400 |
| CGCTACCAGC | GGTGGTTTGT | TTGCCGGATC | AAGAGCTACC | AACTCTTTTT | CCGAAGGTAA 5460 |
| CTGGCTTCAG | CAGAGCGCAG | ATACCAAATA | CTGTCCTTCT | AGTGTAGCCG | TAGTTAGGCC 5520 |
| ACCACTTCAA | GAACTCTGTA | GCACCGCCTA | CATACCTCGC | TCTGCTAATC | CTGTTACCAG 5580 |
| TGGCTGCTGC | CAGTGGCGAT | AAGTCGTGTC | TTACCGGGTT | GGACTCAAGA | CGATAGTTAC 5640 |
| CGGATAAGGC | GCAGCGGTCG | GGCTGAACGG | GGGGTTCGTG | CACACAGCCC | AGCTTGGAGC 5700 |
| GAACGACCTA | CACCGAACTG | AGATACCTAC | AGCGTGAGCA | TTGAGAAAGC | GCCACGCTTC 5760 |
| CCGAAGGGAG | AAAGGCGGAC | AGGTATCCGG | TAAGCGGCAG | GGTCGGAACA | GGAGAGCGCA 5820 |
| CGAGGGAGCT | TCCAGGGGGA | AACGCCTGGT | ATCTTTATAG | TCCTGTCGGG | TTTCGCCACC 5880 |
| TCTGACTTGA | GCGTCGATTT | TTGTGATGCT | CGTCAGGGGG | GCGGAGCCTA | TGGAAAAACG 5940 |
| CCAGCAACGC | GGCCTTTTTA | CGGTTCCTGG | CCTTTTGCTG | GCCTTTGCT | CACATGTTCT 6000 |
| TTCCTGCGTT | ATCCCCTGAT | TCTGTGGATA | ACCGTATTAC | CGCCTTTGAG | TGAGCTGATA 6060 |
| CCGCTCGCCG | CAGCCGAACG | ACCGAGCGCA | GCGAGTCAGT | GAGCGAGGAA | GCGGAAGAGC 6120 |
| GCCCAATACG | CAAACCGCCT | CTCCCCGCGC | GTTGGCCGAT | TCATTAATGC | AGCTGGCACG 6180 |
| ACAGGTTTCC | CGACTGGAAA | GCGGGCAGTG | AGCGCAACGC | AATTAATGTG | AGTTAGCTCA 6240 |
| CTCATTAGGC | ACCCCAGGCT | TTACACTTTA | TGCTTCCGGC | TCGTATGTTG | TGTGGAATTG 6300 |
| TGAGCGGATA | ACAATTTCAC | ACAGGAAACA | GCTATGACCA | TGATTACGCC | 6350 |

( 2 ) INFORMATION FOR SEQ ID NO:9:

( i ) SEQUENCE CHARACTERISTICS:
        ( A ) LENGTH: 6350 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:9:

| | | | | | |
|---|---|---|---|---|---|
| TTCGAAACGA | GAATCCTCAA | AGGATTATGT | AGGGTTTGAG | TTTATATATT | TCGTAAACTG 60 |
| AACAAGATAC | GGGATCCCCC | GCCCCCCTTC | GATTCGGTCG | AAAAAAATTG | TAAATTTTAC 120 |

| | | | | | | |
|---|---|---|---|---|---|---|
| AATTAAGGTA | AAATTTACGT | GTCTACAAAA | ATAAAGTATT | CCCAAAGTTA | CACGTACTTA | 180 |
| CGACGTTATA | AGGACAATGG | TTTCGATCAT | ATTTATTTTT | ATCTATTTGC | ACCTTTAATG | 240 |
| AATCTCAAAG | ACAGTAATTG | CAAAGGAAGG | AGTCAACTGT | TGTATTTACG | CGACGACTCG | 300 |
| TTCGGTCAAA | CGTAGACAGT | CCTAGTTAAA | GGGTAATACG | GTCAGTATAA | TTAATGATCA | 360 |
| GTTAATCAAC | TAAAAATAAA | AACTGTATAT | GTACACTTAC | TTTCTGGGGT | GGACATCCAA | 420 |
| ACCGTTCGAT | CGAATTCATT | GCGGTAAAAC | GTTCCGTACC | TTTTTATGTA | TTGACTCTTA | 480 |
| TCTTTTCAAG | TCTAGTTCCA | GTCCTTGTCT | ACCTTGTCGA | CTTATACCCG | GTTTGTCCTA | 540 |
| TAGACACCAT | TCGTCAAGGA | CGGGGCCGAG | TCCCGGTTCT | TGTCTACCTT | GTCGACTTAT | 600 |
| ACCCGGTTTG | TCCTATAGAC | ACCATTCGTC | AAGGACGGGG | CCGAGTCCCG | GTTCTTGTCT | 660 |
| ACCAGGGGTC | TACGCCAGGT | CGGGAGTCGT | CAAAGATCTC | TTGGTAGTCT | ACAAAGGTCC | 720 |
| CACGGGGTTC | CTGGACTTTA | CTGGGACACG | GAATAAACTT | GATTGGTTAG | TCAAGCGAAG | 780 |
| AGCGAAGACA | AGCGCGCGAA | TACGAGGGGC | TCGAGTTATT | TTCTCGGGTG | TTGGGGAGTG | 840 |
| AGCCCCGCGG | TCAGGAGGCT | AACTGACTCA | GCGGGCCCAT | GGGCACATAG | GTTATTTGGG | 900 |
| AGAACGTCAA | CGTAGGCTGA | ACACCAGAGC | GACAAGGAAC | CCTCCCAGAG | GAGACTCACT | 960 |
| AACTGATGGG | CAGTCGCCCC | CAGAAAGTAA | ACCCCGAGC | AGGCCCTAGC | CCTCTGGGGA | 1020 |
| CGGGTCCCTG | GTGGCTGGGT | GGTGGCCCTC | CATTCGACCG | GTCGTTGAAT | AGACACAGAC | 1080 |
| AGGCTAACAG | ATCACAGATA | CTGACTAAAA | TACGCGGACG | CAGCCATGAT | CAATCGATTG | 1140 |
| ATCGAGACAT | AGACCGCCTG | GGCACCACCT | TGACTGCTCA | AGCCTTGTGG | GCCGGCGTTG | 1200 |
| GGACCCTCTG | CAGGGTCCCT | GAAGCCCCCG | GCAAAAACAC | CGGGCTGGAC | TCAGGATTTT | 1260 |
| AGGGCTAGCA | AATCCTGAGA | AACCACGTGG | GGGGAATCTC | CTCCCTATAC | ACCAAGACCA | 1320 |
| TCCTCTGCTC | TTGGATTTTG | TCAAGGGCGG | AGGCAGACTT | AAAAACGAAA | GCCAAACCCT | 1380 |
| GGCTTCGGCG | CGGCGCGCAG | AACAGACGAC | GTCGTAGCAA | GACACAACAG | AGACAGACTG | 1440 |
| ACACAAAGAC | ATAAACAGAC | TTTTATACCC | GGGCCCGATC | GGACAATGGT | GAGGGAATTC | 1500 |
| AAACTGGAAT | CCAGTGACCT | TTCTACAGCT | CGCCTAGCGA | GTGTTGGTCA | GCCATCTACA | 1560 |
| GTTCTTCTCT | GCAACCCAAT | GGAAGACGAG | ACGTCTTACC | GGTTGGAAAT | TGCAGCCTAC | 1620 |
| CGGCGCTCTG | CCGTGGAAAT | TGGCTCTGGA | GTAGTGGGTC | CAATTCTAGT | TCCAGAAAAG | 1680 |
| TGGACCGGGC | GTACCTGTGG | GTCTGGTCCA | CCCCATGTAG | CACTGGACCC | TTCGGAACCG | 1740 |
| AAAACTGGGG | GGAGGGACCC | AGTTCGGGAA | ACATGTGGGA | TTCGGAGGCG | GAGGAGAAGG | 1800 |
| AGGTAGGCGG | GGCAGAGAGG | GGGAACTTGG | AGGAGCAAGC | TGGGCGGAG | CTAGGAGGGA | 1860 |
| AATAGGTCGG | GAGTGAGGAA | GAGATCCGCG | GGGGTATACC | GGTATACTCT | AGAATATACC | 1920 |
| CCGTGGGGGC | GGGGAACATT | TGAAGGGACT | GGGACTGTAC | TGTTCTCAAT | GATTGTCGGG | 1980 |
| GAGAGAGGTT | CGAGTGAATG | TCCGAGAGAT | GAATCAGGTC | GTGCTTCAGA | CCTCTGGAGA | 2040 |
| CCGCCGTCGG | ATGGTTCTTG | TTGACCTGGC | TGGCCACCAT | GGAGTGGGAA | TGGCTCAGCC | 2100 |
| GCTGTGTCAC | ACCCAGGCGG | CTGTGGTCTG | ATTCTTGGAT | CTTGGAGCGA | CCTTTCCTGG | 2160 |
| AATGTGTCAG | GACGACTGGT | GGGGGTGGCG | GGAGTTTCAT | CTGCCGTAGC | GTCGAACCTA | 2220 |
| TGTGCGGCGG | GTGCACTTCC | GACGGCTGGG | GCCCCACCT | GGTAGGAGAT | CTGACGGTAC | 2280 |
| CGCGCCTAGG | CCTAATCAGG | TTAAACAATT | TCTGTCCTAT | AGTCACCAGG | TCCGAGATCA | 2340 |
| AAACTGAGTT | GTTATAGTGG | TCGACTTCGG | ATATCTCATG | CTCGGTATCT | ATTTTATTTT | 2400 |
| CTAAAATAAA | TCAGAGGTCT | TTTTCCCCCC | TTACTTTCTG | GGGTGGACAT | CCAAACCGTT | 2460 |
| CGATCGAATT | CATTGCGGTA | AAACGTTCCG | TACCTTTTTA | TGTATTGACT | CTTATCTCTT | 2520 |

| | | | | | | |
|---|---|---|---|---|---|---|
| CAAGTCTAGT | TCCAGTCCTT | GTCTACCTTG | TCGACTTATA | CCCGGTTTGT | CCTATAGACA | 2580 |
| CCATTCGTCA | AGGACGGGGC | CGAGTCCCGG | TTCTTGTCTA | CCTTGTCGAC | TTATACCCGG | 2640 |
| TTTGTCCTAT | AGACACCATT | CGTCAAGGAC | GGGGCCGAGT | CCCGGTTCTT | GTCTACCAGG | 2700 |
| GGTCTACGCC | AGGTCGGGAG | TCGTCAAAGA | TCTCTTGGTA | GTCTACAAAG | GTCCCACGGG | 2760 |
| GTTCCTGGAC | TTTACTGGGA | CACGGAATAA | ACTTGATTGG | TTAGTCAAGC | GAAGAGCGAA | 2820 |
| GACAAGCGCG | CGAAGACGAG | GGGCTCGAGT | TATTTTCTCG | GGTGTTGGGG | AGTGAGCCCC | 2880 |
| GCGGTCAGGA | GGCTAACTGA | CTCAGCGGGC | CCATGGGCAC | ATAGGTTATT | TGGGAGAACG | 2940 |
| TCAACGTAGG | CTGAACACCA | GAGCGACAAG | GAACCCTCCC | AGAGGAGACT | CACTAACTGA | 3000 |
| TGGGCAGTCG | CCCCCAGAAA | GTGTGTACGT | CGTACATAGT | TTTAATTAAA | CCAAAAAAAA | 3060 |
| GAATTCATAA | ATGTAATTTA | CCGGTATCAT | GAATTTCAAT | GTAACCGAAG | GAACTTTATT | 3120 |
| TGTACCTCAT | AAGTCTTACA | CAGTATTTAT | AAAGATTAAA | ATTCTATCAT | AGAGGTAACC | 3180 |
| GAAAGATGAA | AAAGAAAATA | AAAAAAAACA | GGAGACAGAA | GGTAAACAAC | AACAACAACA | 3240 |
| AACAAACAAA | CAAACAACCA | ACCAACCAAT | TAAAAAAAAA | TTTCTAGGAT | GTGATATCAA | 3300 |
| GTTCGATCTG | ATAATCGATG | AGACATTGGG | TCCCACTGGA | ACTTCAGTAC | CCATCGGACG | 3360 |
| ACAAAATCGG | AAGGGTGTAG | ATTCTAATGT | CCATACTCGA | TAGTAAAAAC | CATATAACTA | 3420 |
| ACTAACTAAC | TAACTACACA | CACACACACT | AACACAAACA | CACACACTGA | CACTTTTACA | 3480 |
| CACATACCCA | CACACACTTA | CACACATACA | TACACACACA | CACTCACACA | CACACACACA | 3540 |
| CACGTACACA | CACACACACT | GACACAGATA | CACATACTGA | CACACACACA | CACACACACA | 3600 |
| CACACACACA | CACACACACA | CACACAACAC | TTTTTTATAA | GATACCATCA | CTCTCGGTTG | 3660 |
| CGAGGCCGAG | TCCACAGTCC | AACCAAAAAC | TCTGTCTCAG | AAAGTGAATC | GAACCTTAAG | 3720 |
| TGACCGGCAG | CAAAATGTTG | CAGCACTGAC | CCTTTTGGGA | CCGCAATGGG | TTGAATTAGC | 3780 |
| GGAACGTCGT | GTAGGGGGAA | AGCGGTCGAC | CGCATTATCG | CTTCTCCGGG | CGTGGCTAGC | 3840 |
| GGGAAGGGTT | GTCAACGCGT | CGGACTTACC | GCTTACCGCG | GACTACGCCA | TAAAAGAGGA | 3900 |
| ATGCGTAGAC | ACGCCATAAA | GTGTGGCGTA | TACCACGTGA | GAGTCATGTT | AGACGAGACT | 3960 |
| ACGGCGTATC | AATTCGGTCG | GGGCTGTGGG | CGGTTGTGGG | CGACTGCGCG | GGACTGCCCG | 4020 |
| AACAGACGAG | GGCCGTAGGC | GAATGTCTGT | TCGACACTGG | CAGAGGCCCT | CGACGTACAC | 4080 |
| AGTCTCCAAA | AGTGGCAGTA | GTGGCTTTGC | GCGCTACTGC | TTTCCCGGAG | CACTATGCGG | 4140 |
| ATAAAAATAT | CCAATTACAG | TACTATTATT | ACCAAGAAT | CTGCAGTCCA | CCGTGAAAAG | 4200 |
| CCCCTTTACA | CGCGCCTTGG | GGATAAACAA | ATAAAAGAT | TTATGTAAGT | TTATACATAG | 4260 |
| GCGAGTACTC | TGTTATTGGG | ACTATTTACG | AAGTTATTAT | AACTTTTTCC | TTCTCATACT | 4320 |
| CATAAGTTGT | AAAGGCACAG | CGGGAATAAG | GGAAAAAACG | CCGTAAAACG | GAAGGACAAA | 4380 |
| AACGAGTGGG | TCTTTGCGAC | CACTTTCATT | TTCTACGACT | TCTAGTCAAC | CCACGTGCTC | 4440 |
| ACCCAATGTA | GCTTGACCTA | GAGTTGTCGC | CATTCTAGGA | ACTCTCAAAA | GCGGGGCTTC | 4500 |
| TTGCAAAAGG | TTACTACTCG | TGAAAATTTC | AAGACGATAC | ACCGCGCCAT | AATAGGGCAT | 4560 |
| AACTGCGGCC | CGTTCTCGTT | GAGCCAGCGG | CGTATGTGAT | AAGAGTCTTA | CTGAACCAAC | 4620 |
| TCATGAGTGG | TCAGTGTCTT | TTCGTAGAAT | GCCTACCGTA | CTGTCATTCT | CTTAATACGT | 4680 |
| CACGACGGTA | TTGGTACTCA | CTATTGTGAC | GCCGGTTGAA | TGAAGACTGT | TGCTAGCCTC | 4740 |
| CTGGCTTCCT | CGATTGGCGA | AAAACGTGT | TGTACCCCT | AGTACATTGA | GCGGAACTAG | 4800 |
| CAACCCTTGG | CCTCGACTTA | CTTCGGTATG | GTTTGCTGCT | CGCACTGTGG | TGCTACGGAC | 4860 |
| ATCGTTACCG | TTGTTGCAAC | GCGTTTGATA | ATTGACCGCT | TGATGAATGA | GATCGAAGGG | 4920 |

| | | | | | | |
|---|---|---|---|---|---|---|
| CCGTTGTTAA | TTATCTGACC | TACCTCCGCC | TATTTCAACG | TCCTGGTGAA | GACGCGAGCC | 4980 |
| GGGAAGGCCG | ACCGACCAAA | TAACGACTAT | TTAGACCTCG | GCCACTCGCA | CCCAGAGCGC | 5040 |
| CATAGTAACG | TCGTGACCCC | GGTCTACCAT | TCGGGAGGGC | ATAGCATCAA | TAGATGTGCT | 5100 |
| GCCCCTCAGT | CCGTTGATAC | CTACTTGCTT | TATCTGTCTA | GCGACTCTAT | CCACGGAGTG | 5160 |
| ACTAATTCGT | AACCATTGAC | AGTCTGGTTC | AAATGAGTAT | ATATGAAATC | TAACTAAATT | 5220 |
| TTGAAGTAAA | AATTAAATTT | TCCTAGATCC | ACTTCTAGGA | AAAACTATTA | GAGTACTGGT | 5280 |
| TTTAGGGAAT | TGCACTCAAA | AGCAAGGTGA | CTCGCAGTCT | GGGGCATCTT | TTCTAGTTTC | 5340 |
| CTAGAAGAAC | TCTAGGAAAA | AAAGACGCGC | ATTAGACGAC | GAACGTTTGT | TTTTTGGTG | 5400 |
| GCGATGGTCG | CCACCAAACA | AACGGCCTAG | TTCTCGATGG | TTGAGAAAAA | GGCTTCCATT | 5460 |
| GACCGAAGTC | GTCTCGCGTC | TATGGTTTAT | GACAGGAAGA | TCACATCGGC | ATCAATCCGG | 5520 |
| TGGTGAAGTT | CTTGAGACAT | CGTGGCGGAT | GTATGGAGCG | AGACGATTAG | GACAATGGTC | 5580 |
| ACCGACGACG | GTCACCGCTA | TTCAGCACAG | AATGGCCCAA | CCTGAGTTCT | GCTATCAATG | 5640 |
| GCCTATTCCG | CGTCGCCAGC | CCGACTTGCC | CCCCAAGCAC | GTGTGTCGGG | TCGAACCTCG | 5700 |
| CTTGCTGGAT | GTGGCTTGAC | TCTATGGATG | TCGCACTCGT | AACTCTTTCG | CGGTGCGAAG | 5760 |
| GGCTTCCCTC | TTTCCGCCTG | TCCATAGGCC | ATTCGCCGTC | CCAGCCTTGT | CCTCTCGCGT | 5820 |
| GCTCCCTCGA | AGGTCCCCCT | TTGCGGACCA | TAGAAATATC | AGGACAGCCC | AAAGCGGTGG | 5880 |
| AGACTGAACT | CGCAGCTAAA | AACACTACGA | GCAGTCCCCC | CGCCTCGGAT | ACCTTTTGC | 5940 |
| GGTCGTTGCG | CCGGAAAAAT | GCCAAGGACC | GGAAAACGAC | CGGAAAACGA | GTGTACAAGA | 6000 |
| AAGGACGCAA | TAGGGACTA | AGACACCTAT | TGGCATAATG | GCGGAAACTC | ACTCGACTAT | 6060 |
| GGCGAGCGGC | GTCGGCTTGC | TGGCTCGCGT | CGCTCAGTCA | CTCGCTCCTT | CGCCTTCTCG | 6120 |
| CGGGTTATGC | GTTTGGCGGA | GAGGGGCGCG | CAACCGGCTA | AGTAATTACG | TCGACCGTGC | 6180 |
| TGTCCAAAGG | GCTGACCTTT | CGCCCGTCAC | TCGCGTTGCG | TTAATTACAC | TCAATCGAGT | 6240 |
| GAGTAATCCG | TGGGGTCCGA | AATGTGAAAT | ACGAAGGCCG | AGCATACAAC | ACACCTTAAC | 6300 |
| ACTCGCCTAT | TGTTAAAGTG | TGTCCTTTGT | CGATACTGGT | ACTAATGCGG | | 6350 |

( 2 ) INFORMATION FOR SEQ ID NO:10:

( i ) SEQUENCE CHARACTERISTICS:
( A ) LENGTH: 713 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:10:

| | | | | | | |
|---|---|---|---|---|---|---|
| AAGCTTGGGC | TGCAGGTCGA | TCGACTCTAG | AGGATCGATC | CCCACCATGG | GTCAATCACG | 60 |
| CTACCTCCTC | TTTTTGGCCA | CCCTTGCCCT | CCTAAACCAC | CTCAGTTTGG | CCAGGGTCAT | 120 |
| TCCAGTCTCT | GGACCTGCCA | GGTGTCTTAG | CCAGTCCCGA | AACCTGCTGA | AGACCACAGA | 180 |
| TGACATGGTG | AAGACGGCCA | GAGAAAAACT | GAAACATTAT | TCCTGCACTG | CTGAAGACAT | 240 |
| CGATCATGAA | GACATCACAC | GGGACCAAAC | CAGCACATTG | AAGACCTGTT | TACCACTGGA | 300 |
| ACTACACAAG | AACGAGAGTT | GCCTGGCTAC | TAGAGAGACT | TCTTCCACAA | CAAGAGGGAG | 360 |
| CTGCCTGCCC | CCACAGAAGA | CGTCTTTGAT | GATGACCCTG | TGCCTTGGTA | GCATCTATGA | 420 |
| GGACTTGAAG | ATGTACCAGA | CAGAGTTCCA | GGCCATCAAC | GCAGCACTTC | AGAATCACAA | 480 |
| CCATCAGCAG | ATCATTCTAG | ACAAGGGCAT | GCTGGTGGCC | ATCGATGAGC | TGATGCAGTC | 540 |

| | | | | | |
|---|---|---|---|---|---|
| TCTGAATCAT | AATGGCGAGA | CTCTGCGCCA | GAAACCTCCT | GTGGGAGAAG | CAGACCCTTA | 600 |
| CAGAGTGAAA | ATGAAGCTCT | GCATCCTGCT | TCACGCCTTC | AGCACCCGCG | TCGTGACCAT | 660 |
| CAACAGGGTG | ATGGGCTATC | TGAGCTCCGC | CTGAGAATTC | ATTGATCCAC | TAG | 713 |

( 2 ) INFORMATION FOR SEQ ID NO:11:

( i ) SEQUENCE CHARACTERISTICS:
    ( A ) LENGTH: 713 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:11:

| | | | | | |
|---|---|---|---|---|---|
| TTCGAACCCG | ACGTCCAGCT | AGCTGAGATC | TCCTAGCTAG | GGGTGGTACC | CAGTTAGTGC | 60 |
| GATGGAGGAG | AAAAACCGGT | GGGAACGGGA | GGATTTGGTG | GAGTCAAACC | GGTCCCAGTA | 120 |
| AGGTCAGAGA | CCTGGACGGT | CCACAGAATC | GGTCAGGGCT | TTGGACGACT | TCTGGTGTCT | 180 |
| ACTGTACCAC | TTCTGCCGGT | CTCTTTTGA | CTTTGTAATA | AGGACGTGAC | GACTTCTGTA | 240 |
| GCTAGTACTT | CTGTAGTGTG | CCCTGGTTTG | GTCGTGTAAC | TTCTGGACAA | ATGGTGACCT | 300 |
| TGATGTGTTC | TTGCTCTCAA | CGGACCGATG | ATCTCTCTGA | AGAAGGTGTT | GTTCTCCCTC | 360 |
| GACGGACGGG | GGTGTCTTCT | GCAGAAACTA | CTACTGGGAC | ACGGAACCAT | CGTAGATACT | 420 |
| CCTGAACTTC | TACATGGTCT | GTCTCAAGGT | CCGGTAGTTG | CGTCGTGAAG | TCTTAGTGTT | 480 |
| GGTAGTCGTC | TAGTAAGATC | TGTTCCCGTA | CGACCACCGG | TAGCTACTCG | ACTACGTCAG | 540 |
| AGACTTAGTA | TTACCGCTCT | GAGACGCGGT | CTTTGGAGGA | CACCCTCTTC | GTCTGGGAAT | 600 |
| GTCTCACTTT | TACTTCGAGA | CGTAGGACGA | AGTGCGGAAG | TCGTGGGCGC | AGCACTGGTA | 660 |
| GTTGTCCCAC | TACCCGATAG | ACTCGAGGCG | GACTCTTAAG | TAACTAGGTG | ATC | 713 |

( 2 ) INFORMATION FOR SEQ ID NO:12:

( i ) SEQUENCE CHARACTERISTICS:
    ( A ) LENGTH: 215 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
| Met | Gly | Gln | Ser | Arg | Tyr | Leu | Leu | Phe | Leu | Ala | Thr | Leu | Ala | Leu | Leu |
| 1 | | | | 5 | | | | | 10 | | | | | 15 | |
| Asn | His | Leu | Ser | Leu | Ala | Arg | Val | Ile | Pro | Val | Ser | Gly | Pro | Ala | Arg |
| | | | 20 | | | | 25 | | | | | 30 | | | |
| Cys | Leu | Ser | Gln | Ser | Arg | Asn | Leu | Leu | Lys | Thr | Thr | Asp | Asp | Met | Val |
| | | | 35 | | | | 40 | | | | | 45 | | | |
| Lys | Thr | Ala | Arg | Glu | Lys | Leu | Lys | His | Tyr | Ser | Cys | Thr | Ala | Glu | Asp |
| | | 50 | | | | | 55 | | | | 60 | | | | |
| Ile | Asp | His | Glu | Asp | Ile | Thr | Arg | Asp | Gln | Thr | Ser | Thr | Leu | Lys | Thr |
| 65 | | | | | 70 | | | | | 75 | | | | | 80 |
| Cys | Leu | Pro | Leu | Glu | Leu | His | Lys | Asn | Glu | Ser | Cys | Leu | Ala | Thr | Arg |
| | | | | 85 | | | | | 90 | | | | | 95 | |
| Glu | Thr | Ser | Ser | Thr | Arg | Gly | Ser | Cys | Leu | Pro | Pro | Gln | Lys | Thr | |
| | | | 100 | | | | | 105 | | | | | 110 | | |
| Ser | Leu | Met | Met | Thr | Leu | Cys | Leu | Gly | Ser | Ile | Tyr | Glu | Asp | Leu | Lys |
| | | | 115 | | | | | 120 | | | | | 125 | | |

| Met | Tyr | Gln | Thr | Glu | Phe | Gln | Ala | Ile | Asn | Ala | Ala | Leu | Gln | Asn | His |
|---|---|---|---|---|---|---|---|---|---|---|---|---|---|---|---|
| | 130 | | | | | 135 | | | | | 140 | | | | |

| Asn | His | Gln | Gln | Ile | Ile | Leu | Asp | Lys | Gly | Met | Leu | Val | Ala | Ile | Asp |
|---|---|---|---|---|---|---|---|---|---|---|---|---|---|---|---|
| 145 | | | | | 150 | | | | | 155 | | | | | 160 |

| Glu | Leu | Met | Gln | Ser | Leu | Asn | His | Asn | Gly | Glu | Thr | Leu | Arg | Gln | Lys |
|---|---|---|---|---|---|---|---|---|---|---|---|---|---|---|---|
| | | | | 165 | | | | | 170 | | | | | 175 | |

| Pro | Pro | Val | Gly | Glu | Ala | Asp | Pro | Tyr | Arg | Val | Lys | Met | Lys | Leu | Cys |
|---|---|---|---|---|---|---|---|---|---|---|---|---|---|---|---|
| | | | 180 | | | | | 185 | | | | | 190 | | |

| Ile | Leu | Leu | His | Ala | Phe | Ser | Thr | Arg | Val | Val | Thr | Ile | Asn | Arg | Val |
|---|---|---|---|---|---|---|---|---|---|---|---|---|---|---|---|
| | | 195 | | | | | 200 | | | | | 205 | | | |

| Met | Gly | Tyr | Leu | Ser | Ser | Ala | | | | | | | | | |
|---|---|---|---|---|---|---|---|---|---|---|---|---|---|---|---|
| | 210 | | | | | 215 | | | | | | | | | |

( 2 ) INFORMATION FOR SEQ ID NO:13:

( i ) SEQUENCE CHARACTERISTICS:
        ( A ) LENGTH: 1061 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:13:

| | | | | | |
|---|---|---|---|---|---|
| AAGCTTGGGC | TGCAGGTCGA | TCGACTCTAG | AGGATCGATC | CCCACCATGG | GTCCTCAGAA | 60 |
| GCTAACCATC | TCCTGGTTTG | CCATCGTTTT | GCTGGTGTCT | CCACTCATGG | CCATGTGGGA | 120 |
| GCTGGAGAAA | GACGTTTATG | TTGTAGAGGT | GGACTGGACT | CCCGATGCCC | CTGGAGAAAC | 180 |
| AGTGAACCTC | ACCTGTGACA | CGCCTGAAGA | AGATGACATC | ACCTGGACCT | CAGACCAGAG | 240 |
| ACATGGAGTC | ATAGGCTCTG | GAAAGACCCT | GACCATCACT | GTCAAAGAGT | TTCTAGATGC | 300 |
| TGGCCAGTAC | ACCTGCCACA | AGGAGGCGA | GACTCTGAGC | CACTCACATC | TGCTGCTCCA | 360 |
| CAAGAAGGAA | AATGGAATTT | GGTCCACTGA | AATTTTAAAA | AATTTCAAAA | ACAAGACTTT | 420 |
| CCTGAAGTGT | GAAGCACCAA | ATTACTCCGG | ACGGTTCACG | TGCTCATGGC | TGGTGCAAAG | 480 |
| AAACATGGAC | TTGAAGTTCA | ACATCAAGAG | CAGTAGCAGT | TCCCCTGACT | CTCGGGCAGT | 540 |
| GACATGTGGA | ATGGCGTCTC | TGTCTGCAGA | GAAGGTCACA | CTGGACCAAA | GGGACTATGA | 600 |
| GAAGTATTCA | GTGTCCTGCC | AGGAGGATGT | CACCTGCCCA | ACTGCCGAGG | AGACCCTGCC | 660 |
| CATTGAACTG | GCGTTGGAAG | CACGGCAGCA | GAATAAATAT | GAGAACTACA | GCACCAGCTT | 720 |
| CTTCATCAGG | GACATCATCA | AACCAGACCC | GCCCAAGAAC | TTGCAGATGA | AGCCTTTGAA | 780 |
| GAACTCACAG | GTGGAGGTCA | GCTGGGAGTA | CCCTGACTCC | TGGAGCACTC | CCCATTCCTA | 840 |
| CTTCTCCCTC | AAGTTCTTTG | TTCGAATCCA | GCGCAAGAAA | GAAAAGATGA | AGGAGACAGA | 900 |
| GGAGGGGTGT | AACCAGAAAG | GTGCGTTCCT | CGTAGAAGAAG | ACATCTACCG | AAGTCCAATG | 960 |
| CAAAGGCGGG | AATGTCTGCG | TGCAAGCTCA | GGATCGCTAT | TACAATTCCT | CATGCAGCAA | 1020 |
| GTGGGCATGT | GTTCCCTGCA | GGGTCCGATC | CTAGGAATTC | C | | 1061 |

( 2 ) INFORMATION FOR SEQ ID NO:14:

( i ) SEQUENCE CHARACTERISTICS:
        ( A ) LENGTH: 1060 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:14:

-continued

| | | | | | |
|---|---|---|---|---|---|
| TTCGAACCCG | ACGTCCAGCT | AGCTGAGATC | TCCTAGCTAG | GGGTGGTACC | CAGGAGTCTT | 60
| CGATTGGTAG | AGGACCAAAC | GGTAGCAAAA | CGACCACAGA | GGTGAGTACC | GGTACACCCT | 120
| CGACCTCTTT | CTGCAAATAC | AACATCTCCA | CCTGACCTGA | GGGCTACGGG | GACCTCTTTG | 180
| TCACTTGGAG | TGGACACTGT | GCGGACTTCT | TCTACTGTAG | TGGACCTGGA | GTCTGGTCTC | 240
| TGTACCTCAG | TATCCGAGAC | CTTTCTGGGA | CTGGTAGTGA | CAGTTTCTCA | AAGATCTACG | 300
| ACCGGTCATG | TGGACGGTGT | TTCCTCCGCT | CTGAGACTCG | GTGAGTGTAG | ACGACGAGGT | 360
| GTTCTTCCTT | TTACCTTAAA | CCAGGTGACT | TTAAAATTTT | TTAAAGTTTT | TGTTCTGAAA | 420
| GGACTTCACA | CTTCGTGGTT | TAATGAGGCC | TGCCAAGTGC | ACGAGTACCG | ACCACGTTTC | 480
| TTTGTACCTG | AACTTCAAGT | TGTAGTTCTC | GTCATCGTCA | AGGGGACTGA | GAGCCCGTCA | 540
| CTGTACACCT | TACCGCAGAG | ACAGACGTCT | CTTCCAGTGT | GACCTGGTTT | CCCTGATACT | 600
| CTTCATAAGT | CACAGGACGG | TCCTCCTACA | GTGGACGGGT | TGACGGCTCC | TCTGGGACGG | 660
| GTAACTTGAC | CGCAACCTTC | GTGCCGTCGT | CTTATTTATA | CTCTTGATGT | CGTGGTCGAA | 720
| GAAGTAGTCC | CTGTAGTAGT | TTGGTCTGGG | CGGGTTCTTG | AACGTCTACT | TCGGAAACTT | 780
| CTTGAGTGTC | CACCTCCAGT | CGACCCTCAT | GGGACTGAGG | ACCTCGTGAG | GGGTAAGGAT | 840
| GAAGAGGGAG | TTCAAGAAAC | AAGCTTAGGT | CGCGTTCTTT | CTTTTCTACT | TCCTCTGTCT | 900
| CCTCCCCACA | TTGGTCTTTC | CACGCAAGGA | GCATCTCTTC | TGTAGATGGC | TTCAGGTTAC | 960
| GTTTCCGCCC | TTACAGACGC | ACGTTCGAGT | CCTAGCGATA | ATGTTAAGGA | GTACGTCGTT | 1020
| CACCCGTACA | CAAGGGACGT | CCCAGGCTAG | GATCTTAAGG | | | 1060

( 2 ) INFORMATION FOR SEQ ID NO:15:

( i ) SEQUENCE CHARACTERISTICS:
        ( A ) LENGTH: 335 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:15:

| Met | Gly | Pro | Gln | Lys | Leu | Thr | Ile | Ser | Trp | Phe | Ala | Ile | Val | Leu | Leu |
|---|---|---|---|---|---|---|---|---|---|---|---|---|---|---|---|
| 1 | | | | 5 | | | | | 10 | | | | | 15 | |
| Val | Ser | Pro | Leu | Met | Ala | Met | Trp | Glu | Leu | Glu | Lys | Asp | Val | Tyr | Val |
| | | | 20 | | | | 25 | | | | | 30 | | | |
| Val | Glu | Val | Asp | Trp | Thr | Pro | Asp | Ala | Pro | Gly | Glu | Thr | Val | Asn | Leu |
| | | 35 | | | | | 40 | | | | | 45 | | | |
| Thr | Cys | Asp | Thr | Pro | Glu | Glu | Asp | Asp | Ile | Thr | Trp | Thr | Ser | Asp | Gln |
| | 50 | | | | | 55 | | | | | 60 | | | | |
| Arg | His | Gly | Val | Ile | Gly | Ser | Gly | Lys | Thr | Leu | Thr | Ile | Thr | Val | Lys |
| 65 | | | | | 70 | | | | | 75 | | | | | 80 |
| Glu | Phe | Leu | Asp | Ala | Gly | Gln | Tyr | Thr | Cys | His | Lys | Gly | Gly | Glu | Thr |
| | | | | 85 | | | | | 90 | | | | | 95 | |
| Leu | Ser | His | Ser | His | Leu | Leu | Leu | His | Lys | Lys | Glu | Asn | Gly | Ile | Trp |
| | | | | 100 | | | | | 105 | | | | | 110 | |
| Ser | Thr | Glu | Ile | Leu | Lys | Asn | Phe | Lys | Asn | Lys | Thr | Phe | Leu | Lys | Cys |
| | | | 115 | | | | | 120 | | | | | 125 | | |
| Glu | Ala | Pro | Asn | Tyr | Ser | Gly | Arg | Phe | Thr | Cys | Ser | Trp | Leu | Val | Gln |
| | | | 130 | | | | | 135 | | | | | 140 | | |
| Arg | Asn | Met | Asp | Leu | Lys | Phe | Asn | Ile | Lys | Ser | Ser | Ser | Ser | Ser | Pro |
| 145 | | | | | 150 | | | | | 155 | | | | | 160 |

| | | | | | | | | | | | | | | |
|---|---|---|---|---|---|---|---|---|---|---|---|---|---|---|
| Asp | Ser | Arg | Ala | Val<br>165 | Thr | Cys | Gly | Met | Ala<br>170 | Ser | Leu | Ser | Ala | Lys<br>175 |
| Val | Thr | Leu | Asp<br>180 | Gln | Arg | Asp | Tyr | Glu<br>185 | Lys | Tyr | Ser | Val | Ser<br>190 | Cys | Gln |
| Glu | Asp | Val<br>195 | Thr | Cys | Pro | Thr | Ala<br>200 | Glu | Glu | Thr | Leu | Pro<br>205 | Ile | Glu | Leu |
| Ala | Leu<br>210 | Glu | Ala | Arg | Gln | Gln<br>215 | Asn | Lys | Tyr | Glu | Asn<br>220 | Tyr | Ser | Thr | Ser |
| Phe<br>225 | Phe | Ile | Arg | Asp | Ile<br>230 | Ile | Lys | Pro | Asp | Pro<br>235 | Pro | Lys | Asn | Leu | Gln<br>240 |
| Met | Lys | Pro | Leu | Lys<br>245 | Asn | Ser | Gln | Val | Glu<br>250 | Val | Ser | Trp | Glu | Tyr<br>255 | Pro |
| Asp | Ser | Trp | Ser<br>260 | Thr | Pro | His | Ser | Tyr<br>265 | Phe | Ser | Leu | Lys | Phe<br>270 | Phe | Val |
| Arg | Ile | Gln<br>275 | Arg | Lys | Lys | Glu | Lys<br>280 | Met | Lys | Glu | Thr | Glu<br>285 | Glu | Gly | Cys |
| Asn | Gln<br>290 | Lys | Gly | Ala | Phe | Leu<br>295 | Val | Glu | Lys | Thr | Ser<br>300 | Thr | Glu | Val | Gln |
| Cys<br>305 | Lys | Gly | Gly | Asn | Val<br>310 | Cys | Val | Gln | Ala | Gln<br>315 | Asp | Arg | Tyr | Tyr | Asn<br>320 |
| Ser | Ser | Cys | Ser | Lys<br>325 | Trp | Ala | Cys | Val | Pro<br>330 | Cys | Arg | Val | Arg | Ser<br>335 |

(2) INFORMATION FOR SEQ ID NO:16:

(i) SEQUENCE CHARACTERISTICS:
        (A) LENGTH: 61 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:16:

```
CCGCCGGTGG CGGTGGCTCG GGCGGTGGTG GGTCGGGTGG CGGCGGATCT TCCATGGAGC      60
T                                                                       61
```

(2) INFORMATION FOR SEQ ID NO:17:

(i) SEQUENCE CHARACTERISTICS:
        (A) LENGTH: 61 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:17:

```
CCATGGAAGA TCCGCCGCCA CCCGACCCAC CACCGCCCGA GCCACCGCCA CCGGCGGAGC      60
T                                                                       61
```

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:18:

CAGAGTGAAA ATGAAGCT                                                                                            18

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:19:

GAAGCTCTGC ATCCTGCT                                                                                            18

(2) INFORMATION FOR SEQ ID NO:20:

(i) SEQUENCE CHARACTERISTICS:
        (A) LENGTH: 62 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:20:

GGGTCCGATC CGGTGGCGGT GGCTCGGGCG GTGGTGGGTC GGGTGGCGGC GGATCTTCCA      60

TG                                                                                                             62

(2) INFORMATION FOR SEQ ID NO:21:

(i) SEQUENCE CHARACTERISTICS:
        (A) LENGTH: 70 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:21:

GATCCATGGA AGATCCGCCG CCACCCGACC CACCACCGCC CGAGCCACCG CCACCGGATC      60

GGACCCTGCA                                                                                                     70

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:22:

CTATTACAAT TCCTCATG                                                                                            18

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:23:

GAGGGCAAGG GTGGCCAA                                                                                            18

( 2 ) INFORMATION FOR SEQ ID NO:24:

( i ) SEQUENCE CHARACTERISTICS:
        ( A ) LENGTH: 67 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:24:

```
TTGCTGGAGC   TCCGCCGGTG   GCGGTGGCTC   GGGCGGTGGT   GGGTCGGGTG   GCGGCGGATC        60

TATGTGG                                                                            67
```

( 2 ) INFORMATION FOR SEQ ID NO:25:

( i ) SEQUENCE CHARACTERISTICS:
        ( A ) LENGTH: 67 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:25:

```
CACATAGATC   CGCCGCCACC   CGACCCACCA   CCGCCCGAGC   CACCGCCACC   GGCGGAGCTC        60

CAGCAAA                                                                            67
```

( 2 ) INFORMATION FOR SEQ ID NO:26:

( i ) SEQUENCE CHARACTERISTICS:
        ( A ) LENGTH: 82 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:26:

```
CTGGCCTGCA   GGGTCCGATC   CGGTGGCGGT   GGCTCGGGCG   GTGGTGGGTC   GGGTGGCGGC        60

GGATCTAGGG   TCATTCCAGT   CT                                                       82
```

( 2 ) INFORMATION FOR SEQ ID NO:27:

( i ) SEQUENCE CHARACTERISTICS:
        ( A ) LENGTH: 82 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:27:

```
CTGGAATGAC   CCTAGATCCG   CCGCCACCCG   ACCACCACC   GCCCGAGCCA   CCGCCACCGG         60

ATCGGACCCT   GCAGGCCAGA   GA                                                       82
```

( 2 ) INFORMATION FOR SEQ ID NO:28:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:28:

GCAAAGGCGG GAATGTCT 18

( 2 ) INFORMATION FOR SEQ ID NO:29:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:29:

AGGAATAATG TTTCAGTT 18

( 2 ) INFORMATION FOR SEQ ID NO:30:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:30:

CAGCAGTGCA GGAATAAT 18

( 2 ) INFORMATION FOR SEQ ID NO:31:

( i ) SEQUENCE CHARACTERISTICS:
        ( A ) LENGTH: 75 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:31:

CCCTGCAGGG TCCGATCCGG TGGCGGTGGC TCGGGCGGTG GTGGGTCGGG TGGCGGCGGA 60

TCTTCCATGG GTCAA 75

( 2 ) INFORMATION FOR SEQ ID NO:32:

( i ) SEQUENCE CHARACTERISTICS:
        ( A ) LENGTH: 75 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:32:

CCCTGCAGGG TCCGATCCGG TGGCGGTGGC TCGGGCGGTG GTGGGTCGGG TGGCGGCGGA 60

TCTTCCATGG GTCAA 75

( 2 ) INFORMATION FOR SEQ ID NO:33:

( i ) SEQUENCE CHARACTERISTICS:
        ( A ) LENGTH: 96 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:33:

-continued

```
TGTGTTCCCT  GCAGGGTCCG  ATCCGGTGGC  GGTGGCTCGG  GCGGTGGTGG  GTCGGGTGGC         60

GGCGGATCTA  GGGTCATTCC  AGTCTCTGGA  CCTGCC                                     96
```

( 2 ) INFORMATION FOR SEQ ID NO:34:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:34:

```
GTCATCTTCT  TCAGGCGT                                                           18
```

BIOACTIVE FUSION PROTEINS COMPRISING THE P35 AND P40 SUBUNITS OF IL-12

GOVERNMENT SUPPORT

Work described herein was supported by grant No. CA-63399 from the National Cancer Institute. The U.S. Government has certain rights in the invention.

BACKGROUND OF THE INVENTION

Production of therapeutic proteins, such as those which are dimeric, is often difficult, inefficient and expensive. Production of a dimer may require separate expression of the two components, followed by joining of those components to form a functional dimer. Alternative methods of producing functional dimeric proteins would be useful.

SUMMARY OF THE INVENTION

The present invention relates to fusion proteins which comprise at least two polypeptide monomers (chains of amino acids) joined through a polypeptide linker and which are bioactive, as well as to their production. In one embodiment of the present invention, the bioactive fusion proteins of the present invention comprise two or more polypeptides which occur as subunits or monomers in a corresponding bioactive native dimeric protein and are linked through heterologous amino acid residues (amino acid residues which are not present between two subunits in the native protein). As it occurs in nature, IL-12 is a heterodimer made up of a 40 kDa subunit (p40) linked by a disulfide bond to a 35 kDa subunit (p35). Gillessen. S. et al., *Eur. J. Immunology,* 25:200–206 (1995); Ozmen et al., *J. Exp. Med.,* 180:907–915 (1995); Heinsel et al., *Inf. & Immun.,* 62(10):4244–4249 (1994). For example, the fusion protein is a bioactive interleukin-12 (IL-12) fusion protein which comprises two subunits, designated p35 and p40, joined by a polypeptide linker. In further embodiments, the fusion protein comprises the subunits of other dimeric hematopoietic growth factors joined by a polypeptide linker, or the subunits of other dimeric cytokine proteins joined by a polypeptide linker. In another embodiment, the bioactive fusion protein comprises two subunits which are bioactive monomers (e.g., interleukin-2, GMCSF) in their native form and are joined through a polypeptide linker to produce a fusion protein which is chimeric or hybrid in nature in that it comprises at least two components or subunits which do not occur together in a native protein (e.g., an interleukin-2/GMCSF fusion protein).

The present invention also relates to methods of producing the subject fusion proteins, constructs useful in their production and host cells containing the constructs from which the encoded fusion protein is expressed. The subject fusion proteins are expressed in an appropriate expression system, such as by a retrovirus vector which contains and expresses DNA encoding the subunits or monomers and the polypeptide linker as the desired fusion protein in an appropriate host cell, such as in mammalian cells.

Fusion proteins of the present invention are useful for the same purposes (e.g., therapeutic or diagnostic uses) as the corresponding native protein. For example, IL-12 fusion protein can be used to enhance the lytic activity of NK/lymphokine—activated killer cells, act as a growth factor for activated human T and NK cells and stimulate production of IFN-γ by resting peripheral blood mononuclear cells (PBMC). Because of its effects in enhancing cell-mediated immunity, IL-12 is potentially useful for the enhancement of antitumor immunity. The fusion proteins have certain advantages in that they can be made efficiently and reproducibly by the methods described herein.

BRIEF DESCRIPTION OF THE DRAWINGS

FIG. 2 shows the nucleic acid sequences encoding the linker sequences in interleukin-12 fusion proteins of the present invention and flanking IL-12 p35 and Il-12 p40 sequences (SEQ ID NO: 1 to 4), as well as the encoded amino acid sequences (SEQ ID NO: 5 to 7).

Figure 3B:
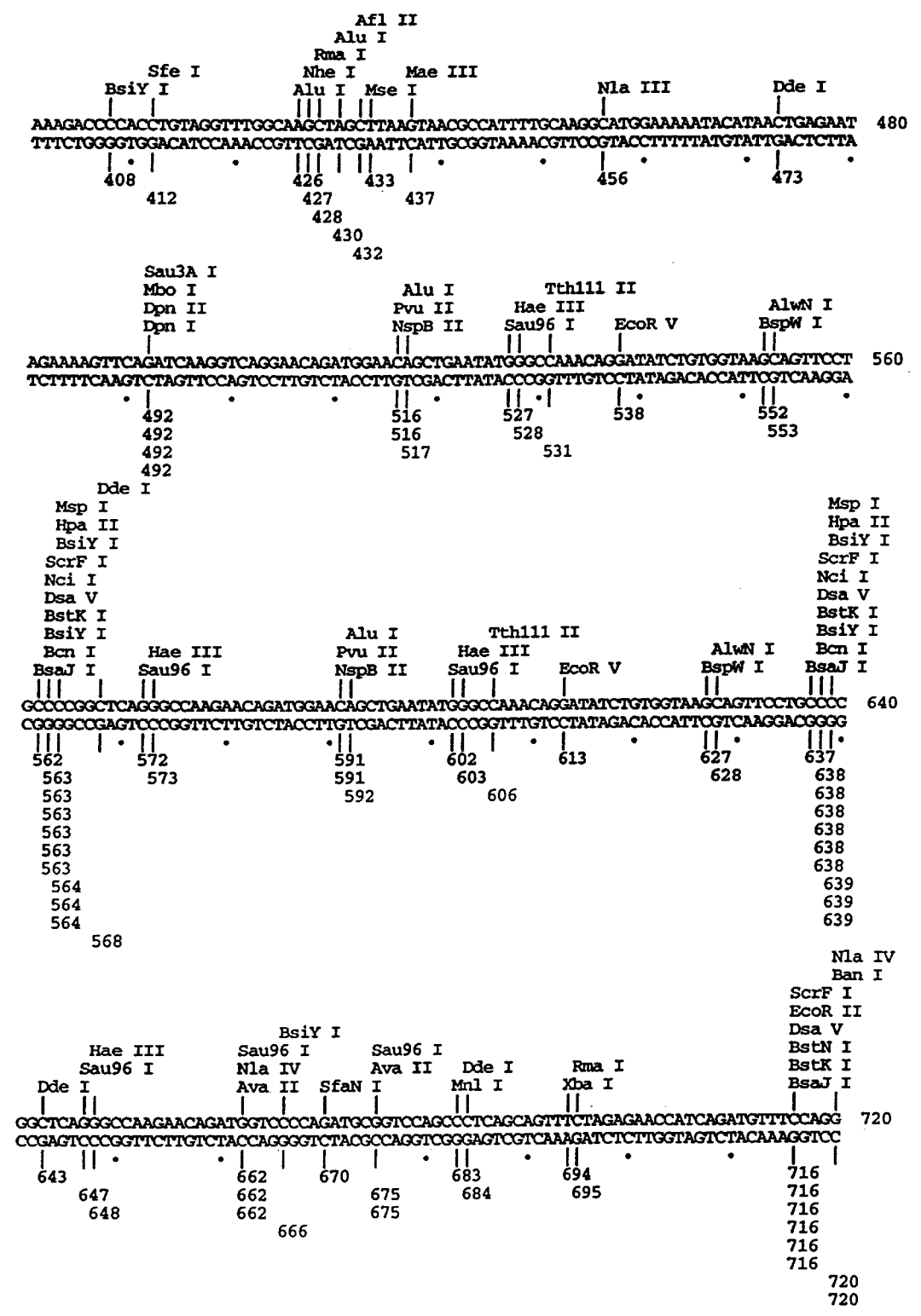
Figure 3C:
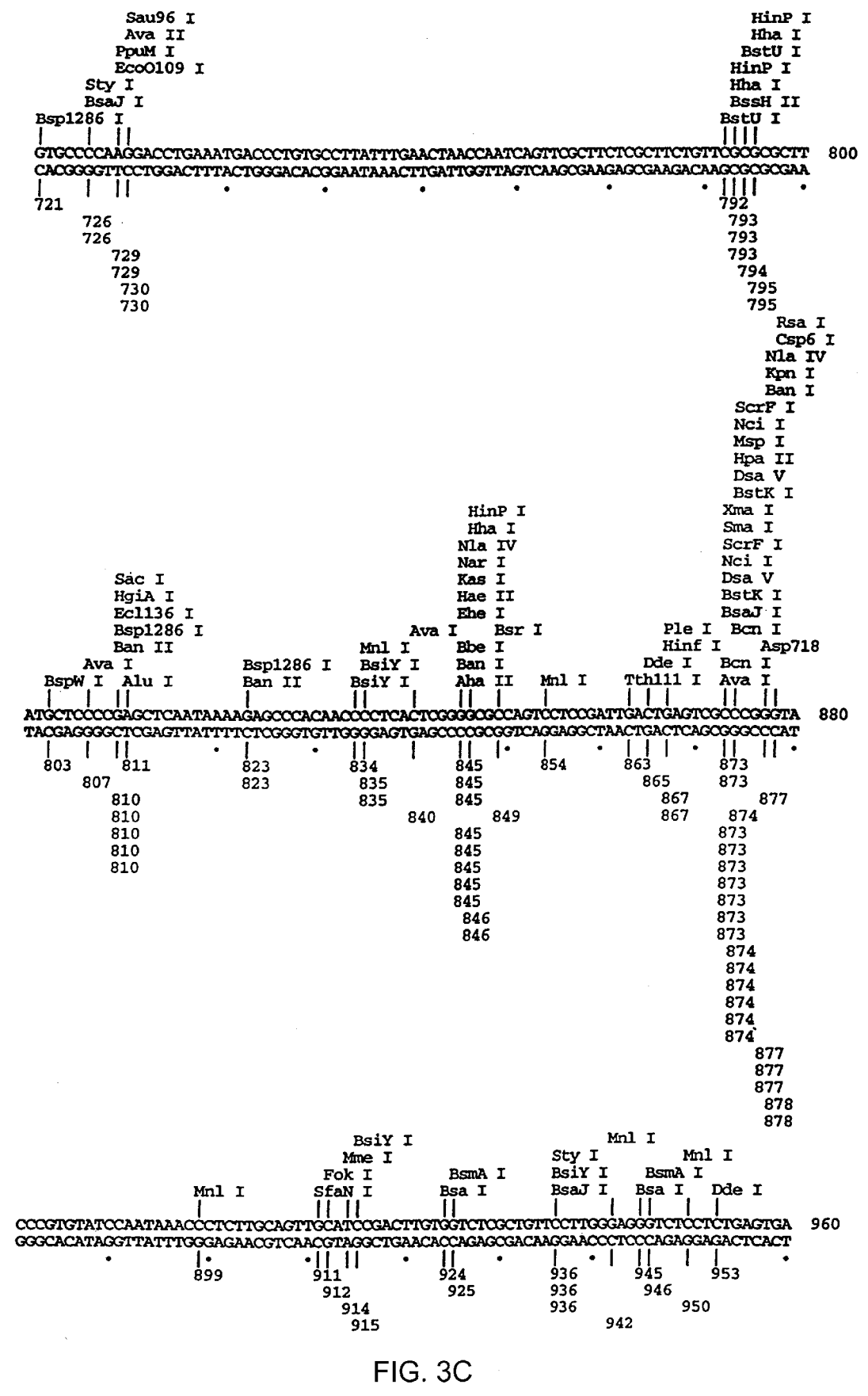
Figure 3D:
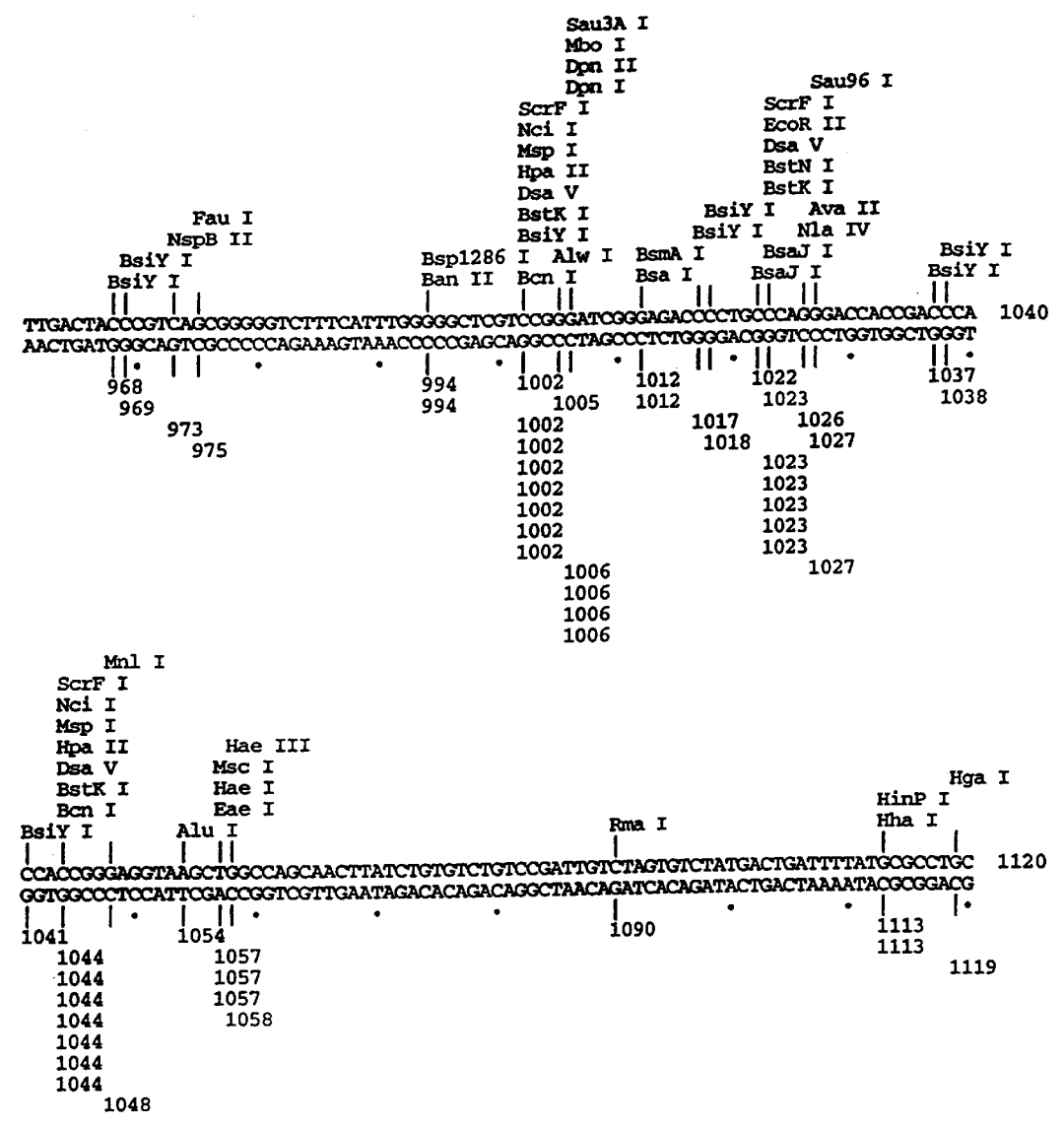
Figure 3E:
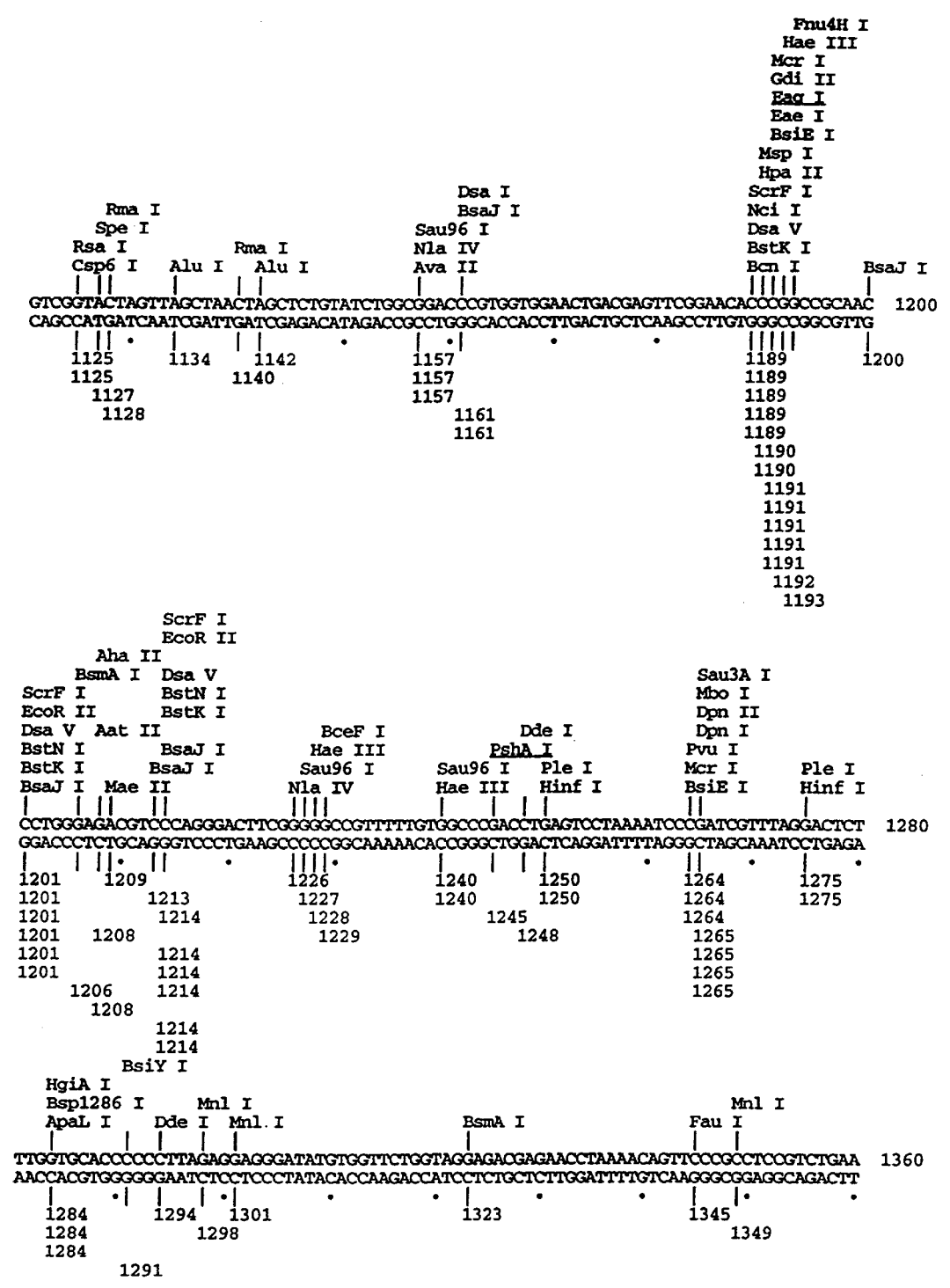
Figure 3G:
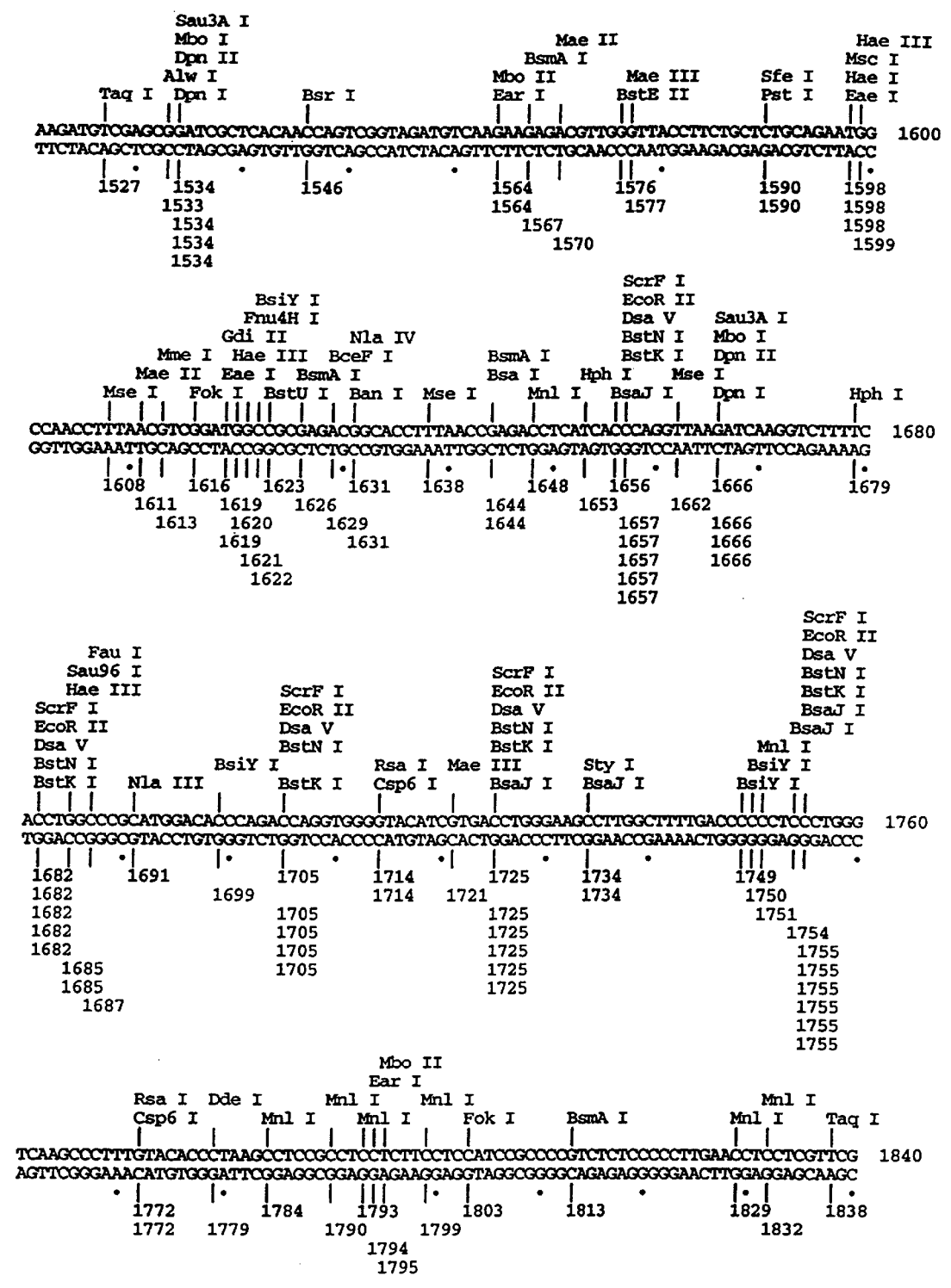
Figure 3H:
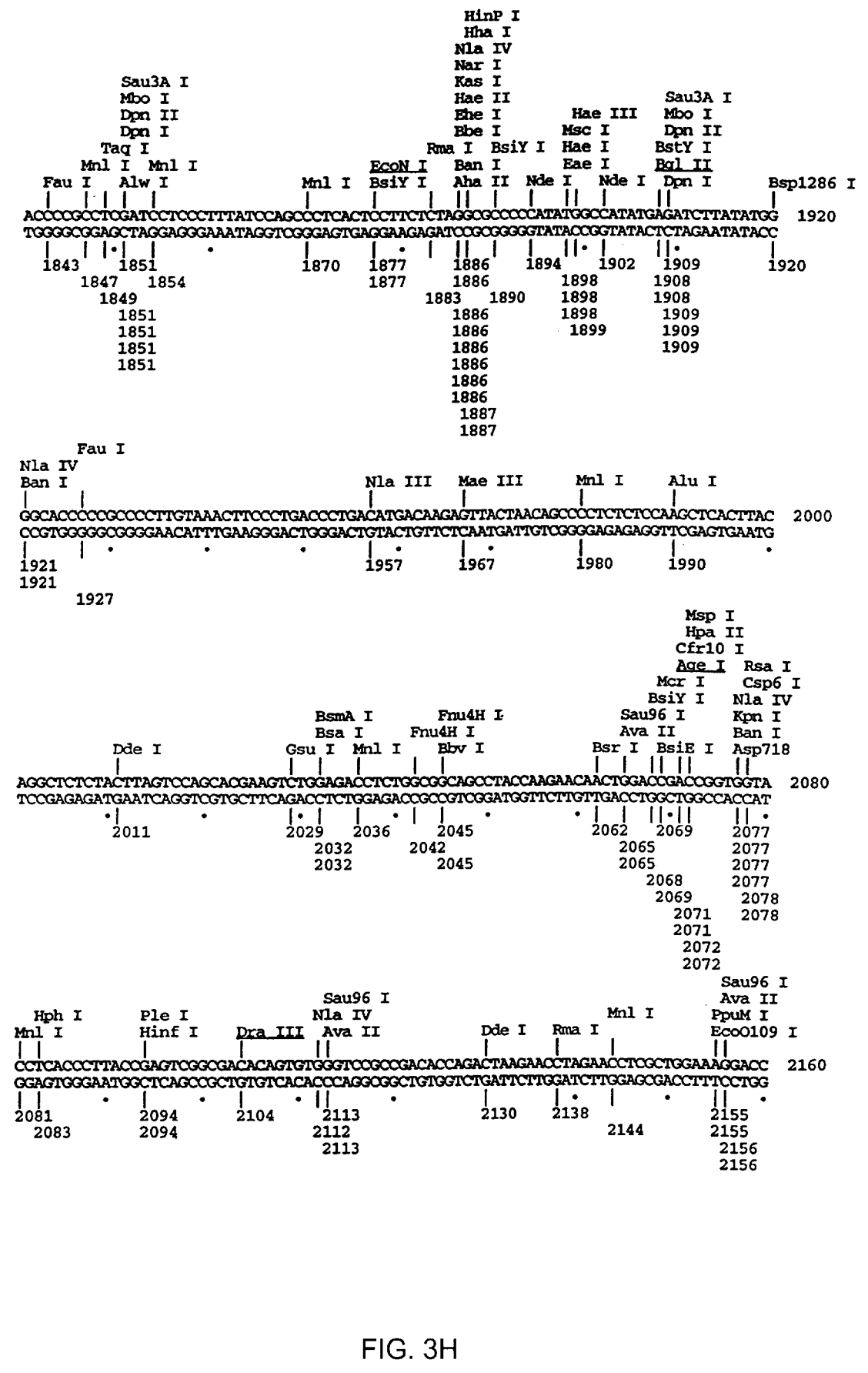
Figure 3J:
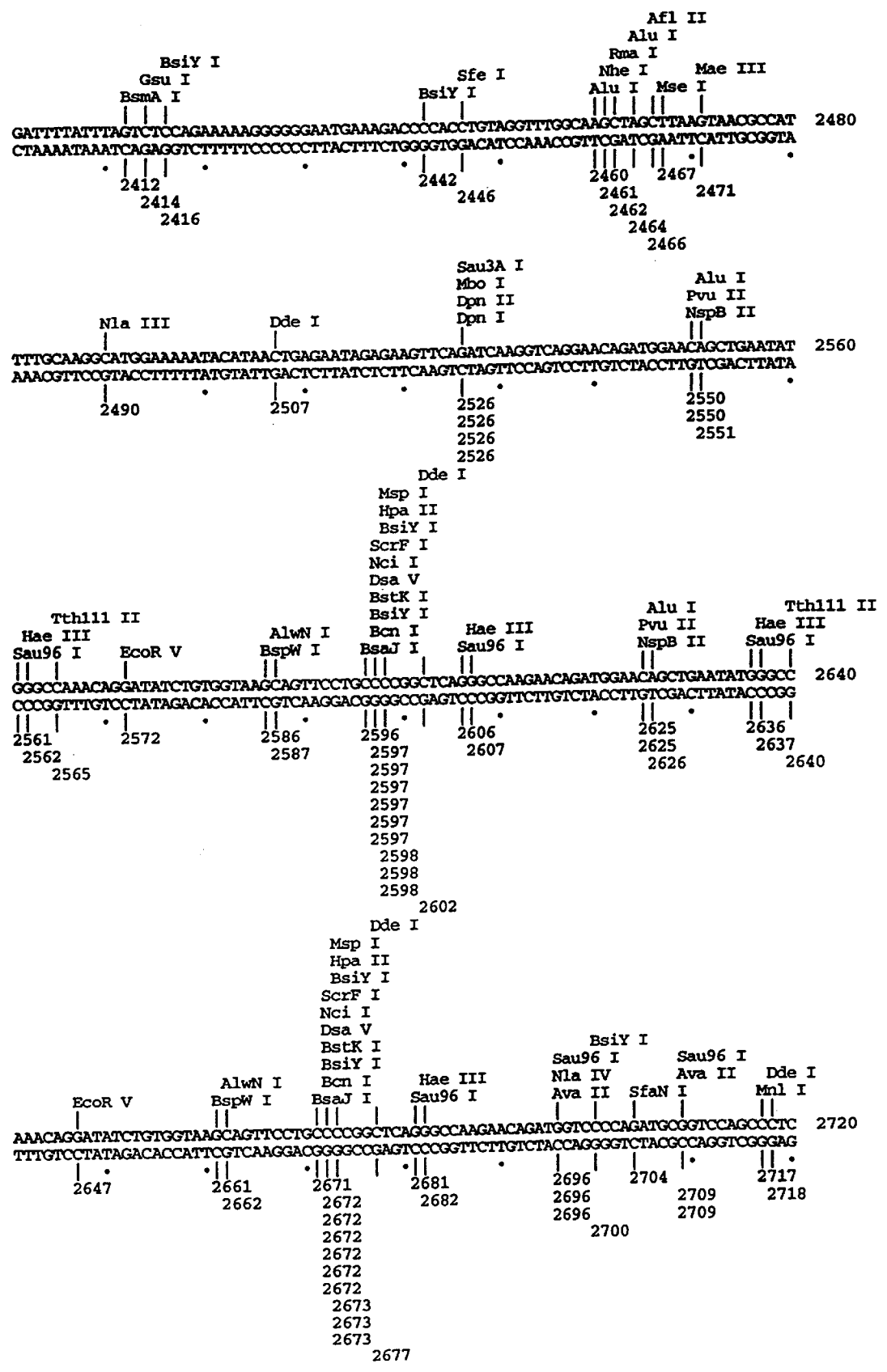
Figure 3M:
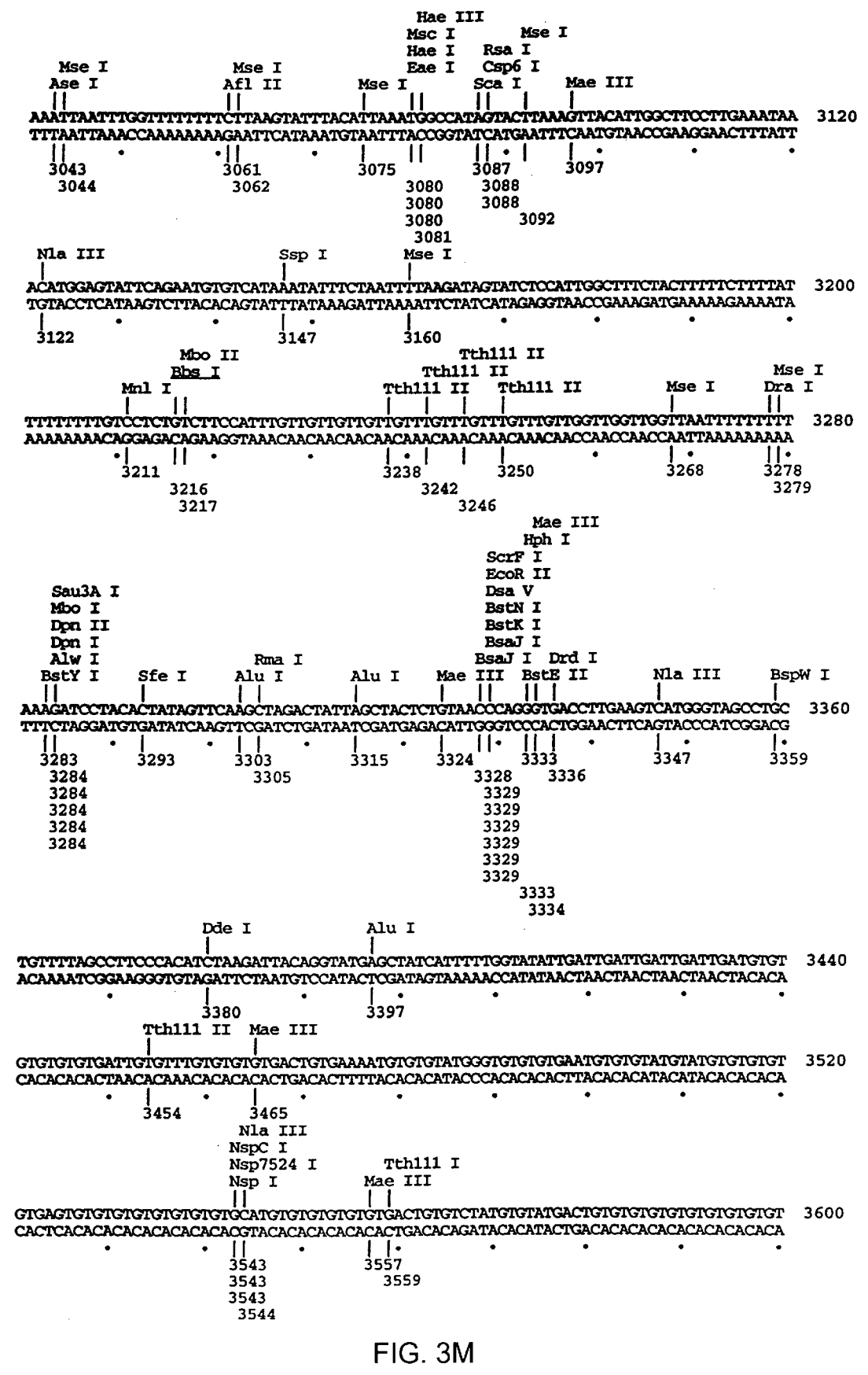
Figure 3N:
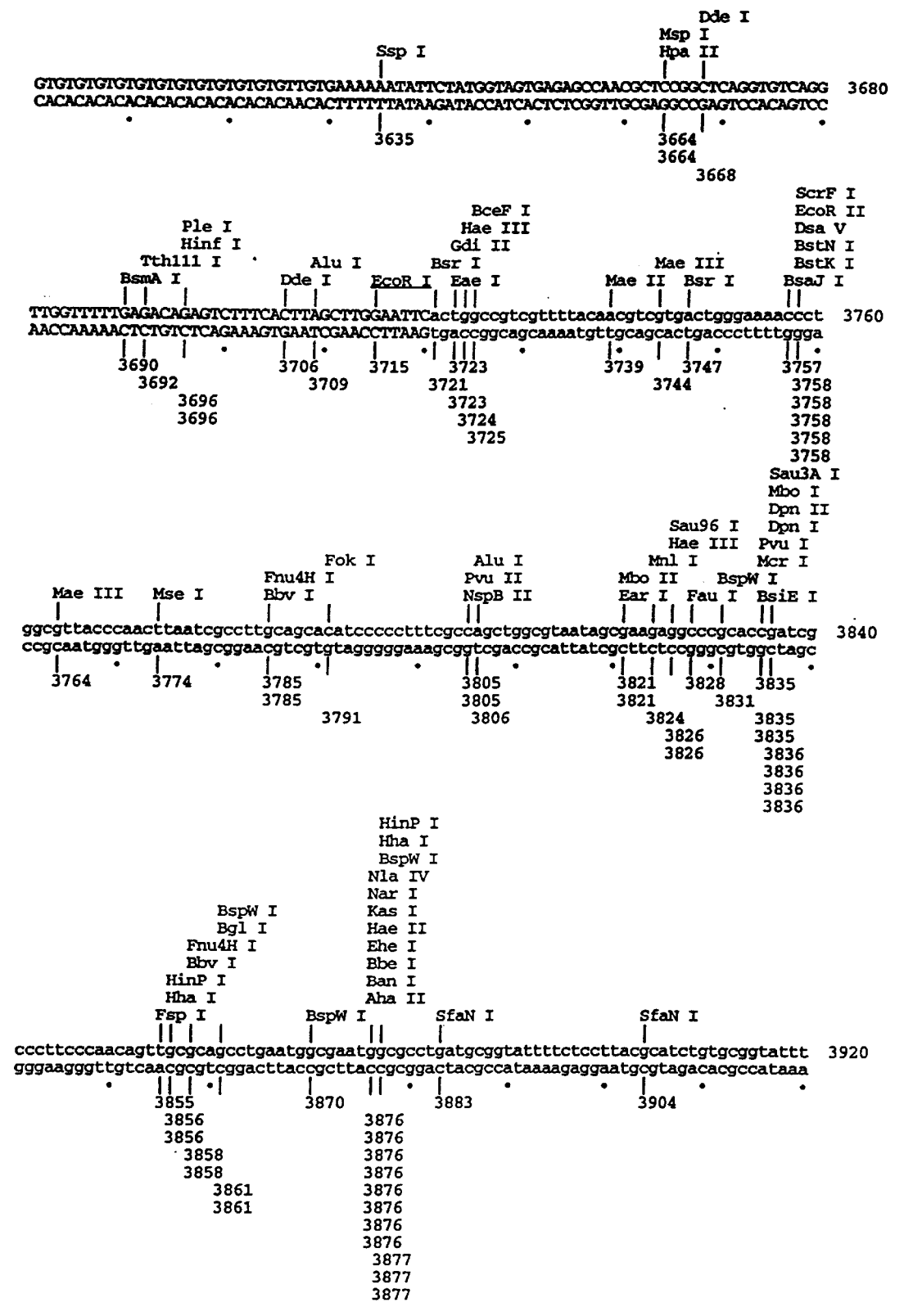
Figure 3P:
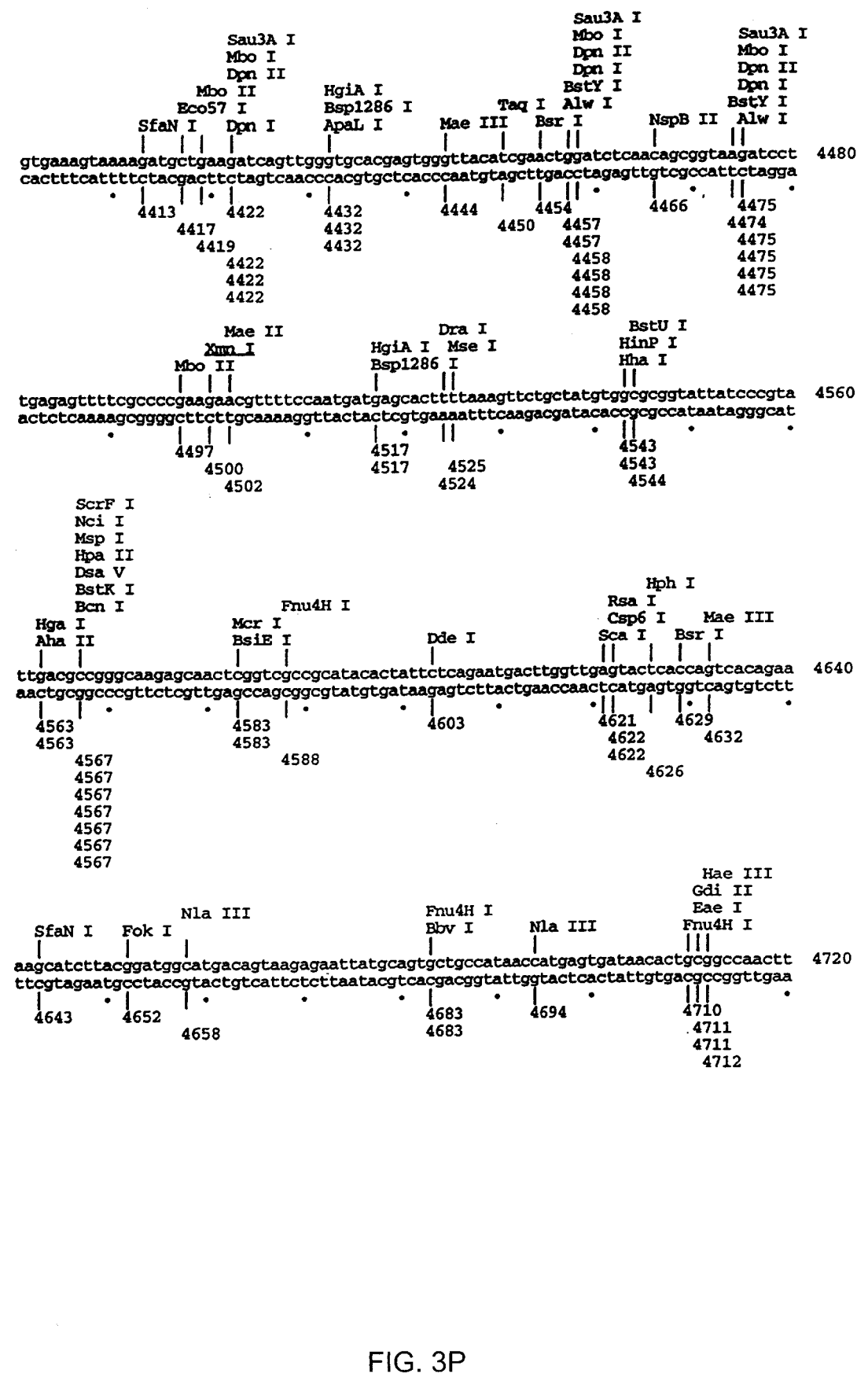
Figure 3S:
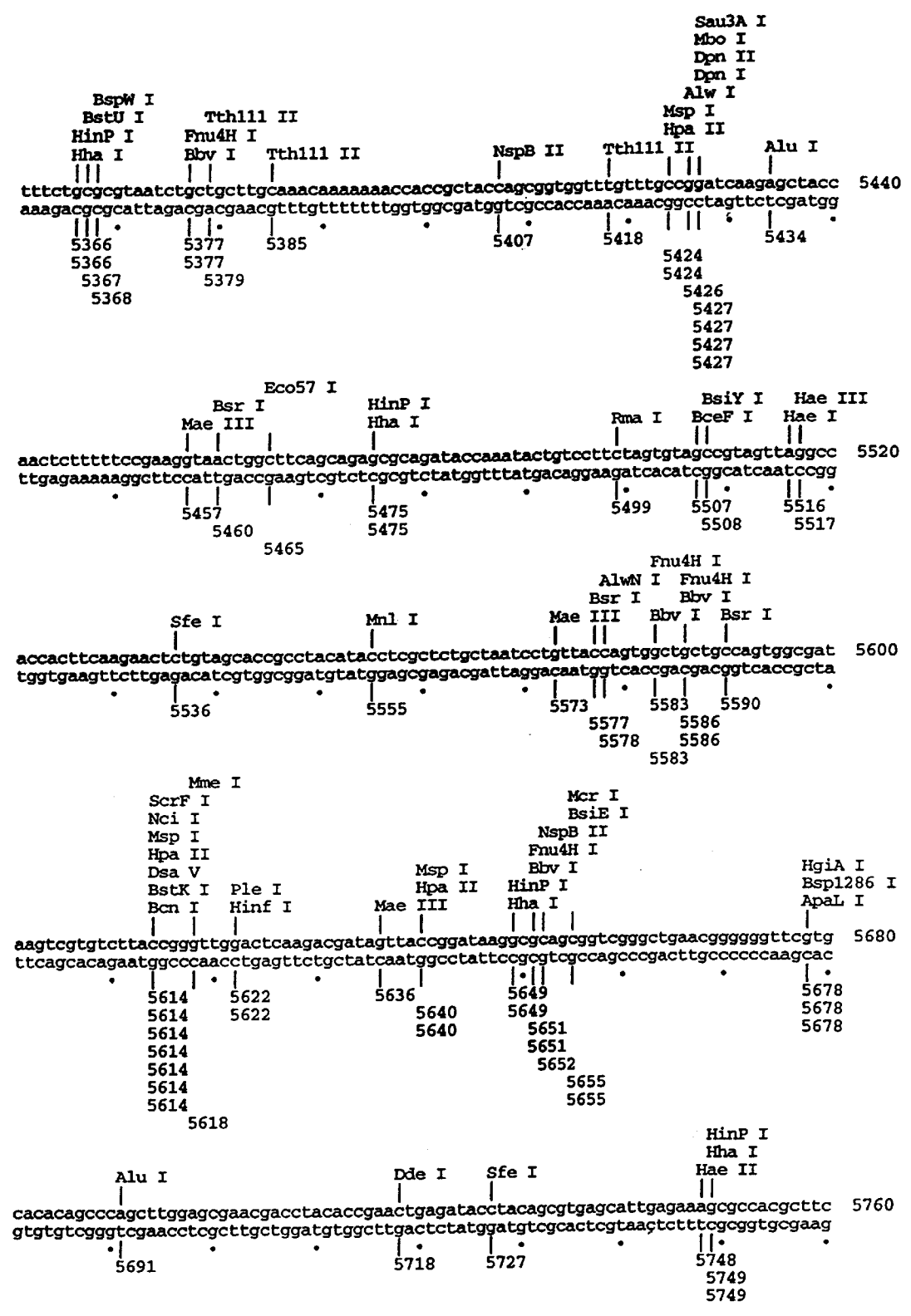
Figure 3T:
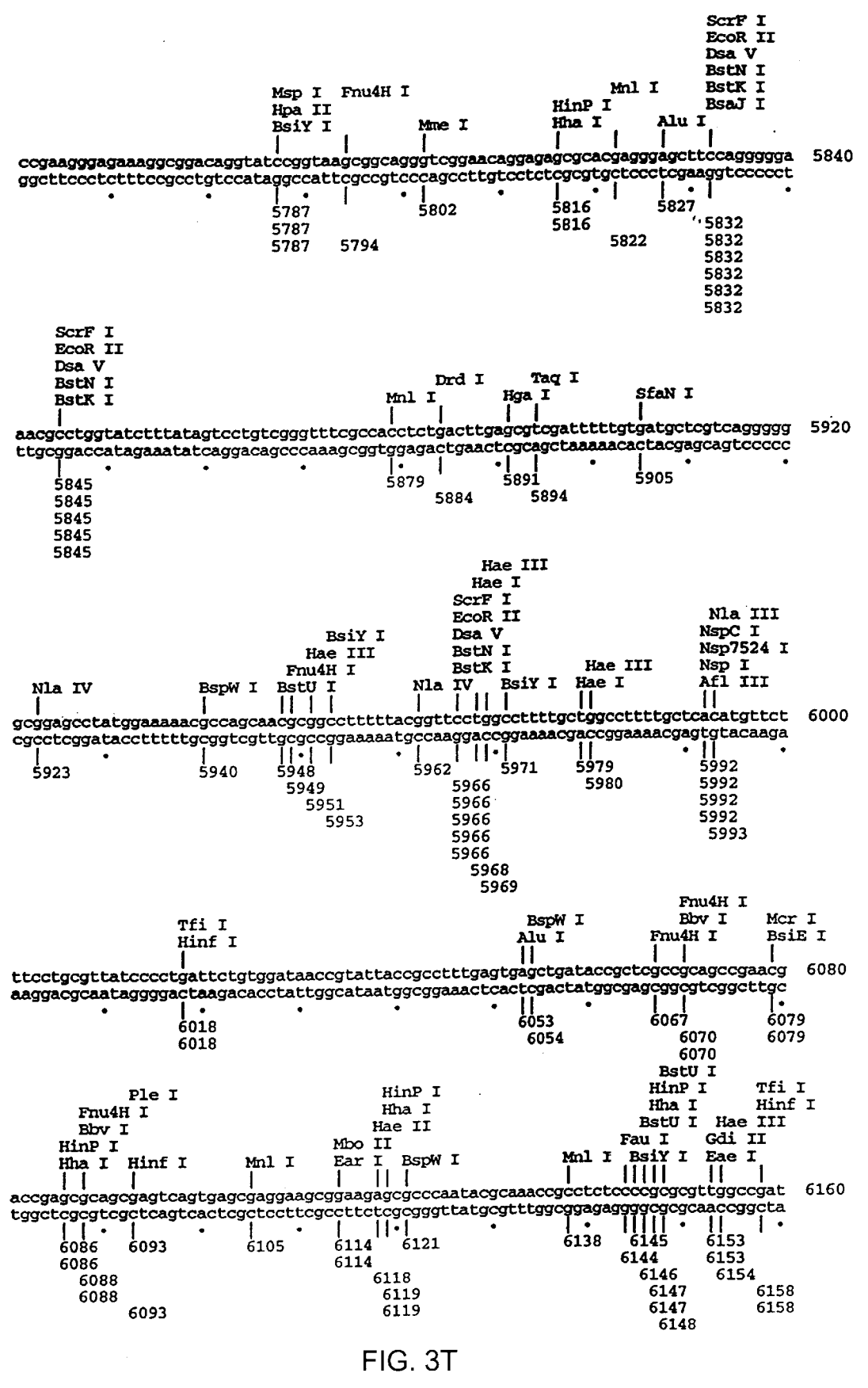

FIG. 3A–3U is the full restriction map and the nucleic acid sequence (SEQ ID NO: 8 and 9) of pUC19-SFG. Each of FIGS. 3A through 3U shows a portion of the complete nucleic acid sequence and restriction map of pUC19-SFG.

FIG. 4A–4C is the nucleic acid sequence (SEQ ID NO:10 and 11) encoding the murine IL-12 p35 subunit and the amino acid sequence of the murine IL-12 p35 subunit (SEQ ID NO: 12). Each of FIGS. 4A through 4C shows a portion of the complete nucleic acid sequence and amino acid sequence of the murine IL-12 p35 subunit.

FIG. 5A–5D is the nucleic acid sequence (SEQ ID NO: 13 and 14) encoding murine IL-12 p40 subunit and the amino acid sequence (SEQ ID NO: 15) of the murine IL-12 p40 subunit. Each of FIGS. 5A through 5D shows a portion of the complete nucleic acid sequence and amino acid sequence of the murine IL-12 p40 subunit.

DETAILED DESCRIPTION OF THE INVENTION

Figure 1:
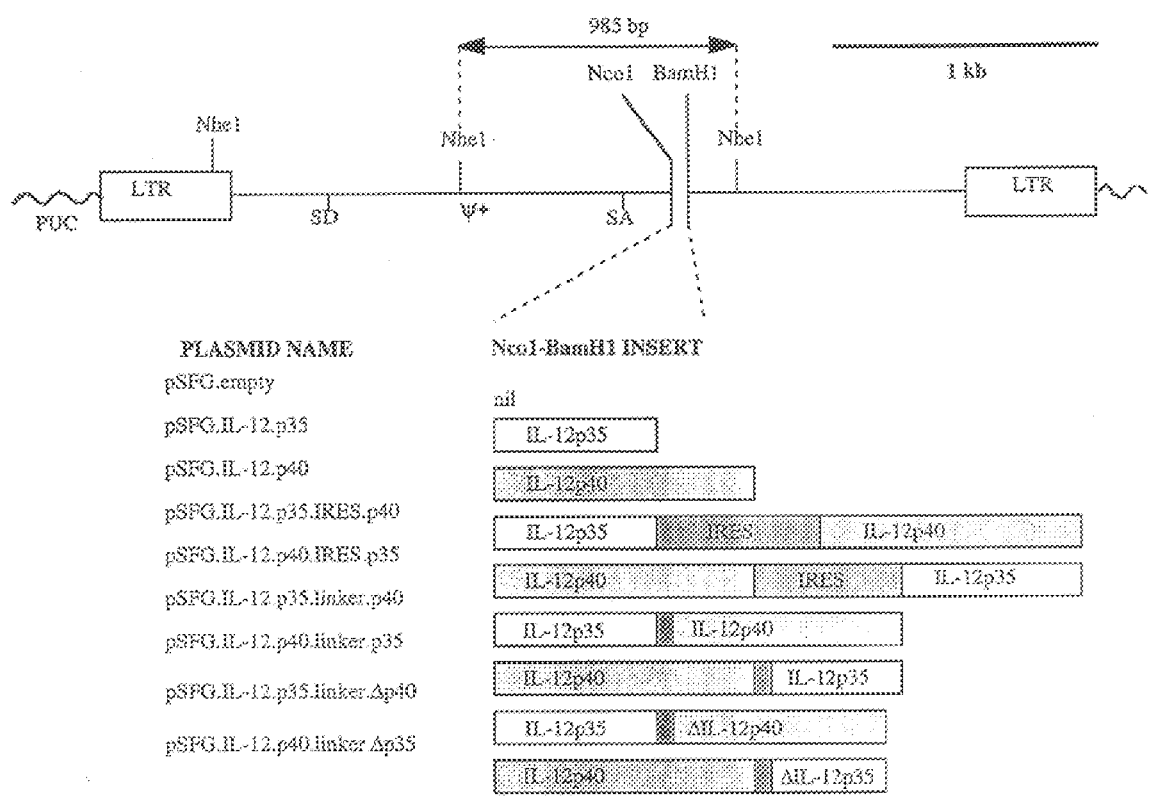
FIG. 1 shows the structures of SFG-based retroviral constructs for interleukin-12 production. (SD=splice donor; IRES=internal ribosome entry site; SA=splice acceptor; LTR-long terminal repeat)
Figure 6:
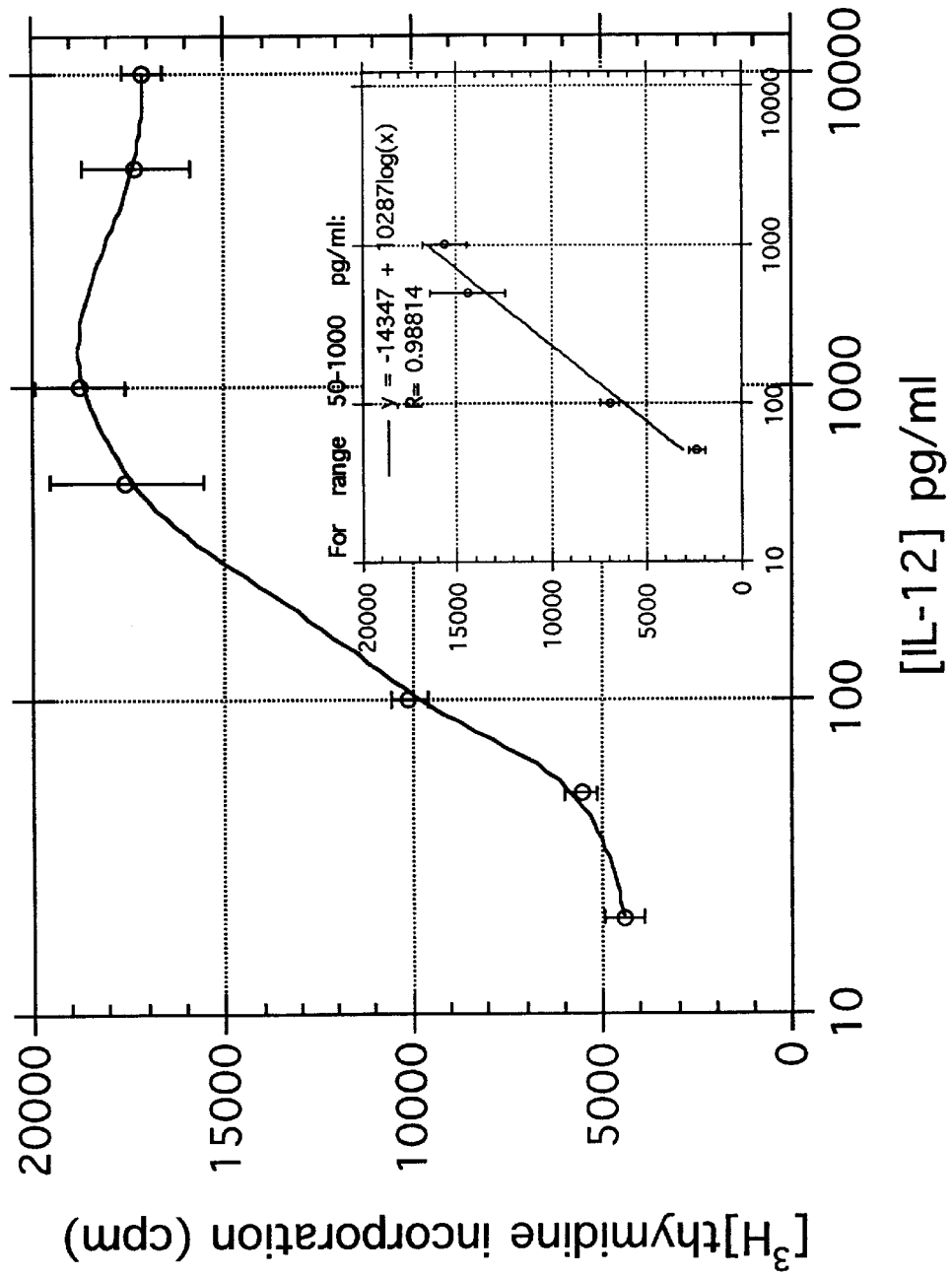
FIG. 6 is a standard curve generated using recombinant murine IL-12.

Described herein are bioactive fusion proteins which comprise two subunits linked or joined by an intervening amino acid linker, a method of producing the bioactive fusion proteins, constructs useful for producing the fusion proteins and host cells containing the constructs, which can be expressed in the host cells.

In one embodiment, the bioactive fusion proteins of the present invention comprise: 1) at least two polypeptide subunits or monomers which correspond to polypeptide subunits present in a native dimeric protein which has a specified bioactivity and 2) at least one polypeptide linker which joins the subunits in such a manner that the resulting fusion protein is bioactive. If the resulting fusion protein is dimeric (includes two subunits or monomers), the two components can be subunits which occur in the same native dimeric protein (e.g., two IL-12 subunits); subunits which occur in two different native dimeric proteins (e.g., one subunit from Il-12 and one subunit from IL-3) or monomers which are bioactive (e.g., IL-2, GMCSF). Multimeric fusion proteins, which comprise three or more subunits joined by polypeptide linkers, can comprise, for example, three or more of the subunits which occur in the same native dimeric protein (e.g., three or more IL-12 subunits), three or more subunits which occur in different native dimeric proteins (e.g., two IL-12 subunits and one IL-3 subunit), three or more bioactive monomers (e.g., three IL-2 monomers, two IL-2 monomers and one GMCSF monomer) or a combination of subunits from native dimeric proteins and bioactive monomers (e.g., two IL-12 subunits and a GMCSF monomer). In each case, a polypeptide linker is present between two subunits (e.g., the order is subunit-linker-subunit-linker-subunit). As used herein, the terms subunit and monomer are used interchangeably to refer to the components of a dimeric or multimeric protein and the single component of a monomeric protein. The order of subunits in the fusion protein of the present invention can be p35-linker-p40 or p40-linker-p35. In either case, the polypeptide linker is positioned between the two subunits. A bioactive fusion protein of the present invention which includes subunits which occur in the same native dimeric protein "mimics" or is similar to what is referred to herein as a corresponding native dimeric protein in terms of its bioactivity, but differs from the corresponding native dimeric protein in that the fusion protein includes linker amino acid residues which do not occur in the corresponding native protein (heterologous amino acid residues) between each pair of polypeptide subunits. A corresponding native protein is one which includes the subunits present in the fusion protein and exhibits biological activity also exhibited by the fusion protein. For example, in the case of a bioactive IL-12 fusion protein, the two subunits, designated p35 and p40, of a mammalian native IL-12 protein(e.g., human, mouse, rat, dog, cat, monkey, chimpanzee, pig IL-12 protein) are joined through a polypeptide linker. Here, the corresponding native protein is the mammalian native IL-12 protein. Similarly, in the case of another bioactive fusion protein, such as IL-3, the corresponding native protein is IL-3. The amino acid residues of the subunits of the bioactive fusion protein can be the same as those of the subunits of the corresponding native protein or can be different, provided that the resulting fusion protein exhibits the desired bioactivity. For example, the subunit(s) can have a different amino acid sequence from that of the corresponding subunit of a native protein (the sequence of the native subunit can differ in that one or more amino acid residues has been deleted or replaced by a naturally-occurring or non-naturally-occurring amino acid residues or in that additional amino acid residues have been incorporated). The desired bioactivity is activity like that of the corresponding native protein (e.g., it produces a physiological response which also results from the activity of the corresponding native protein). The bioactivity of a fusion protein (e.g., the duration of its effect, extent of the resulting response) may be greater or lesser than that of the corresponding native protein.

The polypeptide linker present in the fusion protein can be of any length and composition appropriate to join two subunits in such a manner that the resulting fusion protein has the desired biological activity and retains its integrity as a dimer or multimer. The appropriate length and composition of a linker can be determined empirically for the specific fusion protein to be produced. Generally, the polypeptide linker will be at least 10 amino acid residues. In one embodiment, the polypeptide linker is 11 to 16 amino acid residues and in specific embodiments is 11, 15 or 16 amino acid residues. Specific linkers used in producing bioactive IL-12 fusion proteins are represented in FIG. 2 and described in Example 4. In specific embodiments, the polypeptide linkers have the sequence $(Gly_4Ser)_3$ SEQ ID NO:7; $(Gly_4Ser)_3Ser$ SEQ ID NO:6 or $(Gly_4Ser)_2Ser$ SEQ ID NO:5. These linkers can also be used to join subunits of other fusion proteins. Alternatively, other polypeptide linkers can be used to join two IL-12 subunits to produce a bioactive IL-12 fusion protein.

The DNA encoding the bioactive fusion protein can be cDNA or genomic DNA and can be from a variety of animals, particularly mammals. For example, the DNA can be human, mouse, rat, dog, cat, monkey, chimpanzee, pig or ferret DNA. The DNA can encode a complete or entire subunit (e.g., a complete IL-12 p35 subunit and a complete IL-12 p40 subunit) or a fragment or portion of a subunit(s), provided that the encoded fusion protein has the desired biological activity when it is expressed. The nucleic acid sequences of DNA encoding mouse IL-12 p35 and p40 subunits are represented in FIGS. 4 and 5, respectively. The nucleic acid sequences of DNA encoding human IL-12 p35 and p40 subunits have been published. (See, e.g., Gubler et al. in *Proceedings of the National Academy of Sciences, USA*, 88:4143 (1991)). All or a portion of IL-12 DNA can be used to produce the subject IL-12 fusion protein, provided that the encoded fusion protein is bioactive (has IL-12 activity).

Any expression system appropriate for expressing a fusion protein of the present invention, such as a mammalian, bacterial, yeast or insect expression system, can be used. For example, as described herein, a viral (e.g., a retroviral) vector which expresses DNA (e.g., cDNA) encoding the desired fusion protein in a mammalian host cell has been used. As also described herein, retroviruses containing cDNA encoding the p35 and p40 subunits of IL-12 and an intervening polypeptide linker (an IL-12 fusion protein) have been constructed and transfected into packaging cells (e.g., BOSC23 packaging cells). Target cells (e.g., CMS-5 fibrosarcoma cell line) were infected with virus-containing supernatants and cultured; media conditioned by infected cells was assayed for IL-12 activity using an interleukin-2 and concanavalin-A primed splenocyte proliferation bioassay. Packaging or producer cell lines other than BOSC23 cells can be used to produce infectious retroviruses containing the fusion protein-encodign DNA. In addition, target cells other than a fibrosarcoma cell line can be used to produce the fusion protein. IL-12 bioactivity was demonstrable in cells infected with the retroviruses, as described in Example 4.

Specific retroviruses have been constructed for expression of an IL-12 fusion protein (Example 1 and FIG. 1) and cells infected with the retroviruses have been shown to produce bioactive IL-12 fusion proteins. (See Example 4) The retroviruses used all include the SFG retroviral backbone whose sequence is shown in FIG. 3. The vectors designated pSFG.Il-12.p35 and pSFG.IL-12.p40 include, respectively, the cDNA for the IL-12 p35 subunit or the cDNA for the IL-12 p40 subunit. The vector designated pSFG.IL-12p35-IRES-p40 includes cDNA encoding the IL-12 p35 subunit and cDNA encoding the IL-12 p40 subunit, separated by an internal ribosome entry site sequence. The vector designated pSFG.IL-12p40-IRES-p35 includes the same components as plasmid pSFG.IL-12p35-IRES-p40 but the dimers are in the reverse order, as indicated. The vectors designated pSFG.IL-12.p35 - linker - p40 and pSFG.IL-12.p40 - linker - p35 include cDNAS encoding each IL-12 subunit linked by the $(Gly_4Ser)_2Ser$ and $(Gly_4Ser)_3Ser$ linker respectively. The vectors designated pSFG.IL-l2.p35 - linked - Δp40 and pSFG.IL-12.p40 - linker Δp35 include linked cDNAs in which sequences encoding a putative 22 amino acid leader sequence were deleted from the second cDNA. As described in Example 4, IL-12 bioactivity was shown in conditioned medium from cells infected with the retroviruses.

The present invention is illustrated by the following examples, which are not intended to be limiting in any way.

EXAMPLE 1

Construction of Plasmids

The general structure of the plasmids used in these studies is shown schematically in FIG. 1. The confirmed sequences of the linkers in each of the four fusion proteins are given in FIG. 2.

Source of Plasmids

The plasmids containing cDNAs for the murine IL-12 p35 and p40 subunits (pBS.IL-12.p35 and pBS.IL-12.p40) were provided by Hoffmann-La Roche (Nutley, N.J.). The numbering of base pairs in this document corresponds to the maps of the inserts of these two plasmids (FIGS. 4 and 5). The plasmid containing the SFG retroviral backbone was provided by Dr. Dan Ory (Whitehead Institute, Cambridge, Mass.) as pSFG-TPA, a pUC plasmid containing the SFG retroviral backbone between the HindIII and EcoR1 sites with a tissue plasminogen activator cDNA between the unique Nco1 and BamH1 sites in the SFG retrovirus. A nucleotide sequence map of the SFG retroviral backbone is shown in FIG. 3.

Plasmid pSFG.IL-12.p35

The IL-12p35 cDNA was provided in pBluescript with the sequences surrounding the translational initiation ATG optimized to ACCATGG according to the rules of Kozak. The IL-12p35 cDNA fragment was excised as a Nco1-EcoR1 fragment, the EcoR1 overhang having been filled using the Klenow fragment of *E. coli* DNA polymerase 1. This fragment was ligated using T4 DNA ligase into the Nco1-BamH1 sites of pSFG, the BamH1 overhang having been filled using the Klenow fragment of *E. coli* DNA polymerase 1. The resulting plasmid is designated pSFG.IL-12.p35.

Plasmid pSFG.IL-12.p40

The IL-12p40 cDNA was provided in pBluescript. The Nco1-BamH1 fragment containing the IL-12p40 cDNA was excised and ligated into the Nco1-BamH1 sites of pSFG to make pSFG.IL-12.p40.

General Strategy for Construction of SFG-based Vectors

The general strategy for constructing the SFG-based retroviral vectors for IL-12 fusion protein expression is as follows: Two oligonucleotides encoding the sense and antisense strand of a $(Gly_4Ser)_3$ linker fragment and contiguous IL-12 cDNA sequences to be linked (with terminal sequences for the creation of cohesive ligatable overhangs) were synthesized using a "PCR-mate" 391 DNA synthesizer (Applied Biosystems, Foster City, Calif.). The sequence of the $(Gly_4Ser)_3$ linker was that of Huston et al. (*Proc. Natl. Acad. Sci. USA*, 85:5879–5883(1988)).

For the two fusion proteins using complete IL-12 cDNAs, the oligonucleotides were designed to be cloned into a unique restriction enzyme site at the 3' end of the first cDNA, reconstructing the 3' end of the first cDNA and enabling a Nco1-Nco1 fragment encompassing the full cDNA and linker sequence to be cloned into the Nco1 site of the SFG plasmid containing the other cDNA.

The cloning strategy was similar for the two fusion proteins with a deletion of 66 bp coding the first 22 amino acids of the second cDNA. Linker oligonucleotides were designed to be cloned into unique restriction enzyme sites that lay 3' of bp 66 of the translated bases of the second cDNA in the fusion protein construct. This enabled a fragment to be excised for cloning that reconstructed the 3' end of the first cDNA joined to the linker and contained the linker joined to codon 23 of the second cDNA.

The sequence of the linker and contiguous cDNA regions in plasmids was determined using a "Sequenase" kit (Amersham, Cleveland, Ohio).

Plasmid pSFG.IL-12.p35-linker-p40

The oligonucleotides were: sense, 5'-CCGCC.GGT. GGC.GGT.GGC.TCG.GGC.GGT.GGT.GGG. TCG.GGT.GGC.GG C.GGA.TCT.TCCATGGAGCT-3' (SEQ ID NO: 16); and antisense, 5'-CCATGGA.AGA. TCC.GCC.GCC.ACC.CGA.CCC.ACC.ACC.GC-C.CGA.GCC. ACC.GCC.ACC.GGCGGAGCT-3' (SEQ ID NO: 17).

These two oligonucleotides were annealed, phosphorylated using T4 polynucleotide kinase, and ligated into the Sac1 site of pBS.IL-12.p35 which had been dephosphorylated using calf intestinal phosphatase. The Nco1-Nco1 fragment of the resulting plasmid containing the IL-12p35 cDNA and correctly orientated linker was excised and ligated into the dephosphorylated Nco1 site of pSFG.IL-12p40 to create pSFG.IL-12.p35-linker.p40 (the correct orientation of this ligated fragment was demonstrated by a Sac1 digest).

This plasmid was sequenced using the following two primers: 5'-CAGAGTGAAAATGAAGCT-3' (SEQ ID NO: 18) and 5'-GAAGCTCTGCATCCTGCT-3' (SEQ ID NO: 19), corresponding to bp 601-618 and 613-630 of the IL-12p35 cDNA. Sequencing demonstrated that a deletion had occurred during cloning resulting in a loss of 15 bp from the linker sequences, but maintaining an intact reading frame. The sequence of the linker in this plasmid is given in FIG. 2.

Plasmid pSFG.IL-12.p40.linker.p35

The oligonucleotides were: sense, 5'-GGGTCCGATC-C.GGT.GGC.GGT.GGC.TCG.GGC.GGT.GGT.GGG.TCG. GGT. GGC.GGC.GGA.TCT.TCCATG-3' (SEQ ID NO: 20); and antisense, 5'-GATCCATGGA.AGA.TCC.GCC.GCC. ACC.CGA.CCC.ACC.ACC.GCC.CGA.G CC.ACC.GCC. ACCGGATCGGACCCTGCA-3' (SEQ ID NO: 21).

These two oligonucleotides were annealed and ligated into the Sse83871 and BamH1 sites of pBS.IL-12.p40. The Nco1-Nco1 fragment of the resulting plasmid containing the IL-12p40 cDNA and correctly orientated linker was excised and ligated into the dephosphorylated Nco1 site of pSFG.IL-12p35 to create pSFG.IL-12.p40.linker.p35 (the correct orientation of this ligated fragment was demonstrated by a Xcm1 digest).

This plasmid was sequenced using the following two primers: 5'-CTATTACAATTCCTCATG-3' (SEQ ID NO: 22) and 5'-GAGGGCAAGGGTGGCCAA-3' (SEQ ID NO: 23), corresponding to bp 997-1014 of the IL-12 p40 cDNA and bp 91-74 of the IL-12 p35 cDNA (an antisense primer). Sequencing confirmed that the sequence of the linker and contiguous IL-12 cDNA sequences were as expected.

Subsequent restriction enzyme mapping of pSFG.IL-12.p40.linker.p35 after the transfection and expression studies were completed revealed that it probably contained a concatamer of Nco1-Nco1-fragments from the final cloning step.

Plasmid pSFG.IL-12.p35.linker.Δp40

The oligonucleotides were: sense, 5'-T.TGC. TGG.AGC.TCC.GCC.GGT.GGC.GGT.GGC.TCG.GGC. GGT.GGT.GG G.TCG.GGT.GGC.GGC.GGA.TCT.ATG. TGG-3' (SEQ ID NO: 24) and antisense, 5'-CACAT.AGA.TCC.GCC.GCC.ACC.CGA.CCC.ACC. ACC.GCC.CGA.GCC.ACC.GCC.ACC.GGCGGAGCT. CCAGCAAA-3' (SEQ ID NO: 25).

These two oligonucleotides were annealed, phosphorylated using T4 polynucleotide kinase, and ligated into pBS.IL-12.p40 from which the 30 bp 5' Xcm1-Xcm1 fragment had been excised. The Sac1-Sac1 fragment from the resultant plasmid was excised and ligated into the Sac1 site of pBS.IL-12.p35 which had been dephosphorylated using calf intestinal phosphatase (the correct orientation of the ligated fragment was demonstrated by a Nco1-EcoR1 digest). The Nco1-EcoR1 fragment of the resultant vector was excised, the EcoR1 overhang having been filled using the Klenow fragment of *E. coli* DNA polymerase 1, and ligated into the Nco1 and Klenow-filled BamH1 sites of pSFG to create pSFG.IL-12.p35.linker.Δp40.

This plasmid was sequenced using the following primers: 5'-CAGAGTGAAAATGAAGCT-3'(SEQ ID NO: 18) and 5'-GAAGCTCTGCATCCTGCT-3' (SEQ ID NO: 19), corresponding to bp 601-618 and 613-630 of the IL-12p35 cDNA; and 5'-GTCATCTTCTTCAGGCGT-3' (SEQ ID NO: 34), an antisense primer corresponding to bp 217- 200 of the IL-12 p40 cDNA. Sequencing confirmed that the sequence of the linker and contiguous IL-12 cDNA sequences were as expected.

Plasmid pSFG.IL-12.p40.linker.Δp35

The oligonucleotides were: sense, 5'-CTG.GCC.TGC.AGG.GTC.CGA.TCC- GGT.GGC.GGT.GGC.TCG.GGC.GGT. GGT.GGG.TCG.GGT.GGC.GGC.GGA.TCT- AGG.GTC.ATT.CCA.GTC.T-3' (SEQ ID NO: 26) and antisense, 5'-CTGGAATGACCCT.AGA.TCC.GCC.GCC. ACC.CGA.CCC.ACC.ACC.GCC.CGA.GCC.ACC.GCC. ACC.GGATCGGACCCTGCAGGCCAGAGA-3' (SEQ ID NO: 27).

These two oligonucleotides were annealed, phosphorylated using T4 polynucleotide kinase, and ligated into the PflM1 site in pBS.IL-12.p35 which had been dephosphorylated using calf intestinal phosphatase. (The orientation of this ligated fragment was confirmed by an Sse83871/EcoR1 digest). The Sse83871-EcoR1 fragment from the resultant plasmid was excised, the EcoR1 overhang having been filled using the Klenow fragment of *E. coli* DNA polymerase 1, and ligated into the Sse83871 and Klenow-filled BamH1 sites of pSFG.IL-12.p40 to create pSFG.IL- 12.p40.linker.Δp35.

This plasmid was sequenced using the primer 5'-GCAAAGGCGGGAATGTCT-3' (SEQ ID NO: 28), corresponding to bp 960-977 of the IL-12.p40 cDNA. The sequence of the second linker codon was difficult to read, but its sequence was determined by sequencing the cloned linker in the intermediate plasmid using the antisense primers 5'-AGGAATAATGTTTCAGTT-3' (SEQ ID NO: 29) and 5'-CAGCAGTGCAGGAATAAT-3' (SEQ ID NO: 30) corresponding to bp 224-207 and 233-216 of the IL-12 p35 cDNA respectively. Sequencing confirmed that the sequence of the linker and contiguous IL-12 cDNA sequences were as expected.

Plasmids pSFG.IL-12.p35.IRES.p40 and pSFG.IL-12.p40.IRES.p35

The encephalomyelocarditis virus (ECMV) internal ribosome entry site (IRES) fragment was provided by Dr. Michael Sadelain (Whitehead Institute, Cambridge, Mass.), and was as previously described (Ghattas et al., *Mol. Cell. Biol.*, 11:5848–5859 (1991)).

EXAMPLE 2

Cells and Tissue Culture

BOSC23 packaging cells (Pear et al., *Proc. Natl. Acad. Sci. USA.* 90:8382–8396(1993)) were obtained from Dr. Dirk Lindemann (Whitehead Institute, Cambridge, Mass.). They were passaged in Dulbecco's modified Eagles medium (DMEM) supplemented with 10% calf serum, 50 U/ml penicillin and 50 µg/ml streptomycin.

CMS-5 tumour cells (DeLeo et al., *J. Exp. Med.*, 146:720–734 (1977)) were obtained from Jason Salter (Whitehead Institute, Cambridge, Mass.). They were passaged in DMEM supplemented with 10% foetal calf serum, 50 U/ml penicillin and 50 µg/ml streptomycin. The same medium was used for the collection of CMS-5 conditioned medium.

C57BL/6 splenocytes for IL-12 assays were obtained by mincing a spleen through a sieve (Falcon 2350, Becton Dickinson, Franklin Lakes, N.J.) and collecting the cells in IL-12 medium (as detailed in Schoenhaut et al. (*J. Immunol.*, 148:3433–3440 (1992)) supplemented with 2% foetal calf serum.

EXAMPLE 3

Generation of BOSC23-derived Producer Cells and Collection of Conditioned Media BOSC23 cells were plated at 2×10$^6$ cells per 6 cm tissue culture dish and transfected by CaPO$_4$ transfection with the various constructs as previously described (Pear et al., *Proc. Natl. Acad. Sci. USA,* 90:8382–8396 (1993)). Twenty-four hours after transfection, the medium was replaced with 5ml fresh medium. Virus-containing supernatants were collected 24 h later, filtered through a 0.45 µm filter and polybrene added to a final concentration of 8 µg/ml. 2.5 ml of virus-containing supernatant was used to infect CMS-5 cells immediately for 4 h (in preparation for this infection, CMS-5 cells had been plated at 5×10$^4$ cells/6 cm tissue culture dish the previous day) and the remaining 2.5 ml frozen at −70° C. The following day, the frozen 2.5 ml of virus-containing supernatant was thawed and used for a second 4 h infection of the CMS-5 cells. To collect IL-12-containing conditioned medium, the medium was replaced the following day with 5 ml fresh medium which was harvested 24 h later. These conditioned media were filtered through a 0.2 µm filter and frozen at −70° C. for later assay for IL-12 bioactivity. 5 ml of fresh medium was added to the CMS-5 cells and a second set of conditioned media collected 24 h later which were also filtered and frozen for later assay. The infected CMS-5 cells were then lysed, and genomic DNA prepared for later analysis.

EXAMPLE 4

Bioassay for Murine Interleukin-12

Levels of bioactive interleukin-12 were determined using a concanavalin-A and interleukin-2 primed splenocyte proliferation assay, as described in Schoenhaut et al. (*J. Immunol.*, 148:3433–3440 (1992)). The concanavalin A was obtained commercially from Boehringer (Mannheim, Germany) and the recombinant human interleukin-2 commercially from Chiron Therapeutics (Emeryville, Calif.). To harvest cells for the measurement of [$^3$H]thymidine incorporation into cellular DNA, a Skatron (Sterling, Va.) cell harvester and filtermats (#7031) were used. To assay for inhibitory activity in conditioned media, the 50 μl sample volume comprised 25 μl of 1000 pg/ml recombinant murine IL-12 and 25 μl of the test sample. Samples of conditioned media were assayed in duplicate at several dilutions in the range 1:1 to 1:1000. A standard curve was constructed for each bioassay using recombinant murine IL-12 in the range 20–10,000 pg/ml. The recombinant murine IL-12 was obtained from Hoffmann—La Roche (Nutley, N.J.). To calculate the bioactive IL-12 concentration in test samples in pg/ml, the linear part of the standard curve was approximated using the curve-fit function of "KaleidaGraph 2.1.1" software and the resultant formula used for calculations.

The following constructs (FIG. 1) were assessed for their ability to express a bioactive IL-12 fusion protein:

A. pSFG.IL-12.p35.linker.p40
B. pSFG.IL-12.p40.linker.p35
C. pSFG.IL12-p35.linker.Δp40
D. pSFG.IL12-p40.linker.Δp35

The sequences for the linkers in each construct were as follows, as confirmed by sequencing (some adjacent confirmed IL-12 sequences are given for orientation):

A. 5'->>>IL-12p35.AGC.TCC.GCC-GGT.GGT.GGT.GGG.TCG.GGT.GGC.GGC.GGA.TCT.TCC.ATG.GGT.CCT.CAG.>>>IL-12p40-3' (SEQ ID NO: 1)

B. 5'->>>IL-12p40.CCC.TGC.AGG.GTC.CGA.TCC-GGT.GGC.GGT.GGC.TCG.GGC.GGT.GGT.GGG.TCG.GGT.GGC.GGC.GGA.TCT.TCC.ATG.GGT.CAA.>>>IL-12p35-3'0 (SEQ ID NO: 31)

C. 5'->>>IL-12p35.5'-TAT.CTG.AGC.TCC.GCC-GGT.GGC.GGT.GGC.TCG.GGC.GGT.GGT.GGG.TCG.GGT.GGC.GGC.GGA.TCT.ATG.TGG.GA G.CTG.GAG.AAA.>>>IL-12p40-3' (SEQ ID NO: 32)

D. 5'->>>IL-12p40.TGT.GTT.CCC.TGC.AGG.GTC.CGA.TCC-GGT.GGC.GGT.GGC.TCG.GGC.GGT.GGT.GGG.TCG.GGT.GGC.GGC.GGA.TCT.AGG.GTC.ATT.CCA.GTC.TCT.GGA.CCT.GCC.>>>IL-12p35-3' (SEQ ID NO: 33)

No IL-12 bioactivity was detectable in media conditioned by mock-transfected CMS-5 cells, and CMS-5 cells infected with the SFG retrovirus alone, or by a related retrovirus (MFG) carrying the lac-z gene. However, media conditioned by these cells contained significant inhibitory activity at 1:2 and 1:10 dilutions, inhibiting as much as 95% of the bioactivity of 500 pg/ml of rmIL-12 (Table 1, and other data not shown). Despite this background of inhibitory activity in the conditioned media, bioactive II,-12 production proved to be still demonstrable.

Constructs for the expression of single subunits of the IL-12 protein (pSFG.Il-12.p35 and pSFG.IL-12.p40) resulted in no detectable bioactivity on their own.

However, cotransfection of BOSC23 cells with these constructs together resulted in bioactive IL-12 secretion by infected CMS-5 cells. Similarly, CMS-5 cells infected with the SFG.IL-12.p35 retrovirus and 24 hours later with the SFG.IL-12.p40 retrovirus also produced bioactive IL-12 (Table 1).

The dicistronic constructs designed to express both IL-12 subunits using the IRES sequence resulted in similar levels of bioactive IL-12 production (this was despite an undetectable level of viral infection as determined by Southern hybridization analysis [see below] (Table 1). The ability of IRES-containing retroviruses to result in bioactive IL-12 production has been confirmed by generating stable clonal retrovirus producing cell lines using both these constructs.

All four IL-12 fusion protein constructs resulted in significant bioactive IL-12 production by infected CMS-5 cells. Of particular note was the SFG.IL-12.p40 linker.Δp35 construct, for which IL-12 bioactivity was demonstrable in undiluted conditioned medium (despite the background of substantial inhibitory activity) and for which a 1:1000 dilution of conditioned medium contained bioactivity equivalent to 301 pg/ml of rmIL-12 (Table 1).

All four constructs resulted in titratable IL-12 bioactivity despite significant non-specific inhibitory activity in the conditioned media as well.

TABLE 1

|  | Agonist assay (IL-12 bioactivity, pg/ml) Dilution of CM in assay | | | Antagonist assay (% inhibition of 500 pg/ml IL-12 in assay) Dilution of CM in assay | | |
|---|---|---|---|---|---|---|
| Construct | 1:1 | 1:100 | 1:1000 | 1:2 | 1:10 | 1:1000 |
| No DNA | <50 | <50 | <50 | 56 | 62 | 8.6 |
| SFG-empty | <50 | <50 | <50 | 12 | 47 | -91 |
| MFG-lac-z | <50 | <50 | <50 | 66 | 56 | 64 |
| SFG.IL-12p35 | <50 | <50 | <50 | 65 | 76 | 45 |
| SFG.IL-12p40 | <50 | <50 | <50 | 94 | 84 | 38 |
| 2X infection[a] | 199.7 | 234.2 | 137.2 | 1 | 1 | -84 |
| 2X transfection[b] | 244.7 | 118.8 | <50 | 12 | -3 | -2 |
| A | 86.5 | <50 | <50 | 44 | 60 | 46 |
| B | 253.8 | <50 | <50 | 41 | 12 | -14 |
| C | 189.2 | 57.0 | <50 | 43 | 42 | 47 |
| D | 297.8 | 600.1 | 301.2 | -48 | -143 | -93 |

These data are from one of three separate assays.
[a]Target cells infected sequentially with pSFG.IL-12.p35 and then pSFG.IL-12.p40 viruses (each containing only the respective cDNA between the Nco1 and BamH1 sites)
[b]BOSC23 cells were transfected with a mixture of pSFG.IL-12p35 and pSFG.IL-12.p40 constructs These data indicate IL-12 agonist activity was present in media conditioned by cells infected with the four fusion protein retroviral constructs. It is presumed that this results from bioactivity of secreted respective fusion proteins. The fusion proteins can be demonstrated to be present using known methods, such as Western blotting or immunoprecipitation.

EXAMPLE 5

Southern Hybridization Analysis of Genomic DNA from Infected CMS-5 Cells

Southern hybridization analysis of genomic DNA from the populations of infected CMS-5 cells was performed to demonstrate the presence of a hybridizing band consistent with infection of these cells by retroviruses of the expected structure, and to determine the efficiency of viral infection (by determination of retroviral copy number by genome).

From these Nhe1 digests of genomic DNA, a hybridizing retrovirus-derived band of 985 bp plus the size of the insert cloned into the Nco1-BamH1 sites of SFG was predicted (See FIG. 1). The size of the various cloned fragments were: IL-12.p35 cDNA, 0.6 kb; IL-12.p40 cDNA, 1.0 kb; IRES, 0.7 kb; linker, 0.05 kb; the putative leader sequence deleted in two constructs was 0.066 bp.

The BOSC23 cell supernatants resulted in viral copy numbers of between 0.1 and 1.4 copies/genome (mostly 0.1–0.3 copies/genome) for all constructs except for the IRES-containing constructs, where no hybridizing band of the expected size (3.2 kb) was seen (Table 2).

Of particular note are the comparative results for the IL-12 fusion proteins retrovirus constructs in these populations of infected cells. Although the pSFG.IL-12.p35.linker.p40 retrovirus was present at 1.4 copies/genome, this corresponded with a relatively low level of bioactive IL-12 production (Table 2). However, the SFG.IL-12.p40 linker.Δp35 retrovirus resulted in a relatively high level of IL-12 bioactivity, although it was present at 0.2 copies/genome.

TABLE 2

Retrovirus Copy Number in CMS-5 Cells Infected by SFG.IL-12 Retroviruses

| SFG.IL-12 construct containing: | Retrovirus copy number[a] |
|---|---|
| Nil | 0 |
| IL-12.p35 | 0.1 |
| IL-12.p40 | 0.3 |
| Sequential infection (p35/p40) | 0.3/0.3 |
| Co-transfection (p35/p40) | 0.1/0.1 |
| IL-12.p35-IRES-p40 | <<0.1[b] |
| IL-12.p40.IRES-p35 | <<0.1[b] |
| IL-12.p35.linker.p40 | 1.4[b] |

TABLE 2-continued

Retrovirus Copy Number in CMS-5 Cells Infected by SFG.IL-12 Retroviruses

| SFG.IL-12 construct containing: | Retrovirus copy number[a] |
|---|---|
| IL-12.p40.linker.p35 | 0.1[b] |
| IL-12.p35.linker.Δp40 | 0.4[b] |
| IL-12.p40.linker.Δp35 | 0.2[b] |
| 1 copy control | 1.0[b] |
| 0.1 copy control | 0.1[b] |

[a]Relative to a plasmid copy number control of 13.5 pg of pSFG.IL-12.p35 linker.p40, calculated to be equimolar to 1 copy/genome for 10 μg genomic DNA.
[b]Mean of results from one Southern blot probed first with a p35 and then with a p40 radiolabelled probe. Relative intensity of signals was quantitated using a Fuji BAS-II phosphoimager.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. DNA comprising DNA encoding native IL-12 p35 subunit, DNA encoding a polypeptide linker and DNA encoding native IL-12 p40 subunit, wherein the DNA encoding the polypeptide linker is positioned between the DNA encoding the native IL-12 p35 subunit and the DNA encoding the native IL-12 p40 subunit and wherein expression of the DNA results in production of a bioactive IL-12 fusion protein comprising the native IL-12 p35 subunit and the native IL-12 p40 subunit joined by the encoded polypeptide linker.

2. DNA of claim 1 wherein the native IL-12 p35 subunit and the native IL-12 p40 subunit are of human or mouse origin and the polypeptide linker is selected from the group consisting of: SEQ ID NOS: 5–7.

3. DNA encoding a bioactive IL-12 protein, wherein the bioactive IL-12 protein comprises native IL-12 p35 subunit and native IL-12 p40 subunit joined by a polypeptide linker.

4. DNA of claim 3 wherein the polypeptide linker is selected from the group consisting of: SEQ ID NOS: 5–7.

5. A bioactive IL-12 fusion protein encoded by the DNA of claim 1.

6. A bioactive IL-12 fusion protein encoded by the DNA of claim 2.

7. A bioactive IL-12 encoded by the DNA of claim 3.

8. A bioactive IL-12 protein which comprises native IL-12 p35 subunit and native IL-12 p40 subunit joined by a polypeptide linker.

9. A bioactive IL-12 protein of claim 8 wherein the IL-12 p35 subunit and the IL-12 p40 subunit are of human or mouse origin and the polypeptide linker is 10 to 16 amino acid residues.

10. A bioactive IL-12 protein of claim 9 wherein the polypeptide linker is selected from the group consisting of: SEQ ID NOS: 5–7.

11. An expression vector comprising DNA of claim 1.

12. An expression vector of claim 11 which is a retrovirus vector.

13. An expression vector of claim 12 which is an SFG vector.

14. An expression vector of claim 13 selected from the group consisting of:

a) pSFG.IL-12.p35.linker.p40;
b) pSFG.IL-12.p40.linker.p35;
c) pSFG.IL-12.p35.linker.Δp40 and
d) pSFG.IL-12.p40.linker.Δp35.

15. A method of producing a bioactive IL-12 protein comprising the steps of:

a) providing an expression vector comprising DNA encoding native IL-12 p35 subunit, DNA encoding a polypeptide linker and DNA encoding native IL-12 p40 subunit, wherein the DNA encoding the polypeptide linker is positioned between the DNA encoding the native IL-12 p35 subunit and the DNA encoding the native IL-12 p40 subunit;

b) introducing the expression vector into an appropriate host cell; and c) maintaining the host cell resulting from step (b) under conditions appropriate for expression of the DNA present in the expression vector, resulting in production of a bioactive IL-12 protein in which the two subunits are joined by the polypeptide linker.

16. The method of claim 15, wherein the native IL-12 p35 subunit and the native IL-12 p40 subunit are of human or mouse origin and the polypeptide linker is 10 to 16 amino acid residues.

17. The method of claim 16, wherein the polypeptide linker is selected from the group consisting of: SEQ ID NOS: 5–7.

18. The method of claim 15, wherein the expression vector is a retrovirus vector.

19. The method of claim 18, wherein the expression vector is an SFG vector.

20. The method of claim 19, wherein the SFG vector is selected from the group consisting of:

a) pSFG.IL-12.p35.linker.p40;
b) pSFG.IL-12.p40.linker.p35;
c) pSFG.IL-12.p35.linker.Δp40 and
d) pSFG.IL-12.p40.linker.Δp35.

* * * * *

UNITED STATES PATENT AND TRADEMARK OFFICE
CERTIFICATE OF CORRECTION

PATENT NO. : 5,891,680
DATED : April 6, 1999
INVENTOR(S) : Graham J. Lieschke
Richard C. Mulligan It is certified that error appears in the above-identified patent and that said Letters Patent is hereby corrected as shown below:

On Column 41, line 44, Claim 7, after "IL-12" insert the word --protein--.

Signed and Sealed this

Twenty-eighth Day of September, 1999

Attest:

Q. TODD DICKINSON

*Attesting Officer*   *Acting Commissioner of Patents and Trademarks*